United States Patent [19]

Hubschwerlen et al.

[11] Patent Number: 5,637,579

[45] Date of Patent: Jun. 10, 1997

[54] PENAM DERIVATIVES

[75] Inventors: Christian Hubschwerlen, Durmenach, France; Hans Richter, Grenzach-Wyhlen, Germany; Jean-Luc Specklin, Kembs, France

[73] Assignee: Hoffmann-La Roche Inc., Nutley, N.J.

[21] Appl. No.: 293,865

[22] Filed: Aug. 22, 1994

[30] Foreign Application Priority Data

Aug. 24, 1993 [CH] Switzerland ............... 2511/93
May 31, 1994 [CH] Switzerland ............... 1687/94

[51] Int. Cl.$^6$ ............ C07D 499/897; A61K 31/43
[52] U.S. Cl. ............ 514/192; 514/195; 540/310
[58] Field of Search ............ 540/310; 514/192, 514/195

[56] References Cited

U.S. PATENT DOCUMENTS

| | | | |
|---|---|---|---|
| 4,282,236 | 8/1981 | Broom | 540/310 |
| 4,331,677 | 5/1982 | Foglio et al. | 424/270 |
| 4,365,174 | 12/1982 | Barth | 424/114 |
| 4,863,914 | 9/1989 | Perrone et al. | 540/310 |
| 5,132,300 | 7/1992 | Voekmann et al. | 540/310 |

FOREIGN PATENT DOCUMENTS

| | | |
|---|---|---|
| 236 074 | 9/1987 | European Pat. Off. . |
| 272 016 | 6/1988 | European Pat. Off. . |

OTHER PUBLICATIONS

Douglas, James L., et al., *Canadian Journal of Chemistry*, 62:2282–2286 (1984).

Foglio, Maurizio, et al., *Heterocycles*, 15(2):785–789 (1981).

Baldwin, Jack E., *Tetrahedron*, vol. 43, No. 5, pp. 1003–1012 (1987).

Baldwin, J.E., et al., *Tetrahedron*, vol. 46, No. 17, pp. 6145–6154 (1990).

Nishimura, S., et al., *The Journal of Antibiotics*, vol. XLII, No. 1, pp. 159–162 (Jan. 1989).

*Primary Examiner*—Mukund J. Shah
*Assistant Examiner*—King Lit Wong
*Attorney, Agent, or Firm*—George W. Johnston; Dennis P. Tramaloni; Alan P. Kass

[57] ABSTRACT

The present invention discloses compounds having the formula

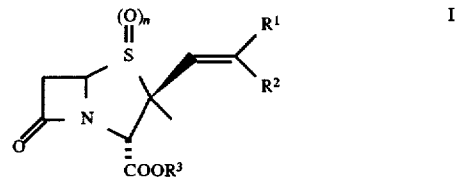

wherein
one of $R^1$ and $R^2$ is —$COR^4$, —CN, —$CH_2R^5$, halogen, —CH=$CHR^6$ or Q and the other is hydrogen or lower alkyl or both $R^1$ and $R^2$ together form a γ-lactam ring,
$R^3$ is hydrogen, lower alkyl, aryl-alkyl, allyl or a residue which is cleavable in vivo,
$R^4$ is hydrogen, lower alkyl, lower alkoxy, benzyloxy, amino, lower alkylamino or lower alkyl-lower alkoxyamino,
$R^5$ is hydroxy, —$OCONHR^7$, —$OCONH_2$ or a five- or six-membered hetero-aromatic ring which contains N,S and/or O and which is linked via a nitrogen atom,
$R^6$ is —CN or CHO,
$R^7$ is —$COCH_2Cl$,
Q is a five- or six-membered hetero-aromatic ring which contains N, S and/or O and
n is 0, 1 or 2,
and the pharmaceutically compatible salts thereof.

These compounds are good β-lactamase inhibitors. They can be used for the prevention or treatment of bacterial infections, optionally together with a β-lactam antibiotic.

45 Claims, No Drawings

PENAM DERIVATIVES

The present invention relates to penam derivatives and, in particular, is concerned with compounds having the formula

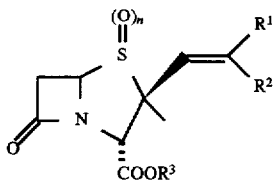

wherein
one of $R^1$ and $R^2$ is —$COR^4$, —CN, —$CH_2R^5$, halogen, —CH=$CHR^6$ or Q and the other is hydrogen or lower alkyl or both $R^1$ and $R^2$ together form a γ-lactam ring, $R^3$ is hydrogen, lower alkyl, aryl-alkyl, allyl or a residue which is cleavable in vivo, $R^4$ is hydrogen, lower alkyl, lower alkoxy, benzyloxy, amino, lower alkylamino or lower alkyl-lower alkoxyamino, $R^5$ is hydroxy, —$OCONHR^7$, —$OCONH_2$, or a five- or six-membered hetero-aromatic ring which contains at least one heteroatom selected from N, S and O and which is linked via a nitrogen atom, $R^6$ is —CN or CHO, $R^7$ is —$COCH_2Cl$, Q is a five- or six-membered hetero-aromatic ring which contains at least one heteroatom selected from N, S and O and n is 0, 1 or 2, and the pharmaceutically compatible salts thereof.

These compounds are novel and are distinguished by therapeutically valuable properties. In particular, they have pronounced β-lactamase inhibiting properties and are accordingly useful in combination with β-lactam antibiotics such as the penicillins and cephalosporins in the control of pathogens which form β-lactamase.

Furthermore, they have an antibacterial activity of their own against certain bacterial strains, such as, for example, Acinetobacter spp.

The term "lower alkyl", alone or in combination such as "lower alkoxy" or "lower-alkylamino", signifies straight-chain or branched saturated hydrocarbon residues with a maximum of 7, preferably a maximum of 4, carbon atoms such as, for example, methyl, ethyl, isopropyl or t-butyl.

The term "aryl-alkyl" embraces benzyl, benzhydryl, p-methoxybenzyl or p-nitrobenzyl, and the like.

The term "halogen" embraces fluorine, chlorine, bromine or iodine.

The term "five- or six-membered hetero-aromatic ring which contains at least one heteroatom selected from N, S and O" preferably signifies 2-pyridyl, 1-methyl-pyridin-2-ylio, 1,3-thiazol-2-yl, 1,2,4-oxadiazol-3-yl, 2-thiazolyl, 2-pyridinyl, and the like.

A residue which is cleavable in vivo signifies a residue which is suitable for oral administration and which preferably contains an ester group such as, for example, —$CH_2OOCC(CH_3)_3$,

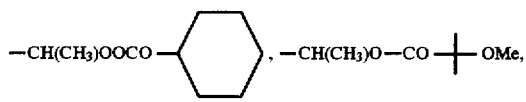

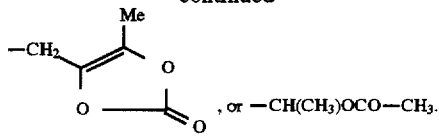

Objects of the present invention include 3β-alkenyl-penam derivatives of formula I and pharmaceutically compatible salts thereof and as pharmaceutically active substances, the making of these compounds, medicaments containing a compound of formula I or a pharmaceutically compatible salt and, if desired, additionally a β-lactam antibiotic and the making of such medicaments, as well as the use of compounds of formula I and of pharmaceutically compatible salts thereof in the control or prevention of illnesses, especially of bacterial infections in both human and non-human hosts, and, respectively, for the making of corresponding medicaments.

Furthermore, compounds having the formula

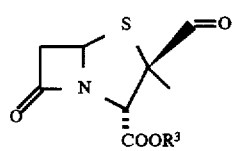

wherein $R^3$ is as defined above, are an object of the invention.

These compounds of formula II are important intermediates for the making of the compounds of formula I.

Those compounds of formula I in which $R^1$=CN, halogen or $COR^4$ and $R^4$=amino, methyl, lower alkoxy or benzyloxy and $R^2$=hydrogen, for example, the following compounds, are especially preferred:

Benzhydryl (E/Z)-(2S,3S,5R)-3-(2-cyanoethenyl)-3-methyl-7-oxo-4-thia-1-aza-bicyclo [3.2.0]heptane-2-carboxylate, benzhydryl (E)-(2S,3S,5R)-3-(2-cyanoethenyl)-3-methyl-4,4,7-trioxo-4-thia-1-aza-bicyclo[3.2.0]heptane-2-carboxylate, benzhydryl (Z)-(2S,3S,5R)-3-(2-cyanoethenyl)-3-methyl-4,4,7-trioxo-4-thia-1-aza-bicyclo[3.2.0]heptane-2-carboxylate sodium (E)-(2S,3S,5R)-3-(2-cyanoethenyl)-3-methyl-4,4,7-trioxo-4-thia-1-aza-bicyclo[3.2.0]heptane-2-carboxylate sodium (Z)-(2S,3S,5R)-3-(2-cyanoethenyl)-3-methyl-4,4,7-trioxo-4-thia-1-aza-bicyclo[3.2.0]heptane-2-carboxylate, sodium (Z)-(2S,3S,5R)-3-(2-chloro-vinyl)-3-methyl-4,4,7-trioxo-4-thia-1-aza-bicyclo[3.2.0]heptane-2-carboxylate, sodium(E)-(2S,3S,5R)-3-methyl-3-(3-oxo-but-1-enyl)-4,4,7-trioxo-4-thia-1-aza-bicyclo[3.2.0]heptane-2-carboxylate.

Furthermore, the following compounds are also especially preferred:

Benzhydryl (E/Z)-(2S,3S,5R)-3-(2-carbamoyl-vinyl)-3-methyl-7-oxo-4-thia-1-aza-bicyclo[3.2.0]heptane-2-carboxylate, benzhydryl (E)-(2S,3S,5R)-3-(2-carbamoyl-vinyl)-3-methyl-4,4,7-trioxo-4-thia-1-aza-bicyclo [3.2.0]heptane-2-carboxylate, benzhydryl (Z)-(2S,3S,5R)-3-(2-carbamoyl-vinyl)-3-methyl-4,4,7-trioxo-4-thia-1-aza-bicyclo[3.2.0]heptane-2-carboxylate, sodium (E)-(2S,3S,5R)-3-(2-carbamoyl-vinyl)-3-methyl-4,4,7-trioxo-4-thia-1-aza-bicyclo[3.2.0]heptane-2-carboxylate, sodium (Z)-(2S,3S,5R)-3-(2-carbamoyl-vinyl)-3-methyl-4,4,7-trioxo-4-thia-1-aza-bicyclo[3.2.0]heptane-2-carboxylate, benzhydryl (E)-(2S,3S,5R)-3-(2-ethoxycarbonyl-vinyl)-3methyl-7-oxo-4-thia-1-aza-bicyclo[3.2.0]heptane-2-carboxylate, benzhydryl (E)-(2S,3S,5R)-3-(2-ethoxycarbonyl-vinyl)-3-methyl-4,4,7-trioxo-4-thia-1-aza-bicyclo[3.2.0]heptane-2carboxylate, sodium (E)-(2S,3S,5R)-3-(2-ethoxycarbonyl-vinyl)-3-methyl-4,4,7-trioxo-4-thia-1-aza-bicyclo[3.2.0]heptane-2-carboxylate, benzhydryl (E)-(2S,3S,5R)-3-(2-benzyloxycarbonyl-vinyl)-3-methyl- 7-oxo-4-thia-1-aza-bicyclo[3.2.0]heptane-2-carboxylate, benzhydryl (E)-(2S,3S,5R)-3-(2-benzyloxycarbonyl-vinyl)-3-methyl-4,4,7-trioxo-4-thia-1-aza-bicyclo[3.2.0]heptane-2-carboxylate, sodium (E)-(2S,3S,5R)-3-(2-benzyloxycarbonyl-vinyl)-3-methyl-4,4,7-trioxo-4-thia-1-aza-bicyclo[3.2.0]heptane-2-carboxylate.

The 3β-alkenyl-penam derivatives of formula I as well as their pharmaceutically compatible salts can be made in accordance with the invention by a) reacting a compound of the formula

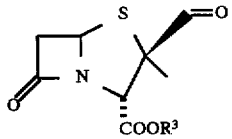

wherein $R^3$ is as defined above, with a compound of the formula

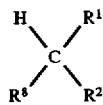

wherein $R^1$ and $R^2$ are as defined above and $R^8 = P^{\oplus}(aryl)_3$, $PO(Oalkyl)_2$, $Si(alkyl)_3$ or halogen, in the presence of an activating agent, or b) oxidizing a compound of formula I in which n signifies 0, or c) converting a compound of formula I in which $R^3$ is different from hydrogen into the corresponding free acid, and d) if desired, converting an acidic compound of formula I into a pharmaceutically acceptable salt.

Scheme 1 shows two known methods (Wittig or Horner reaction) for carrying out process variant a).

Scheme 1

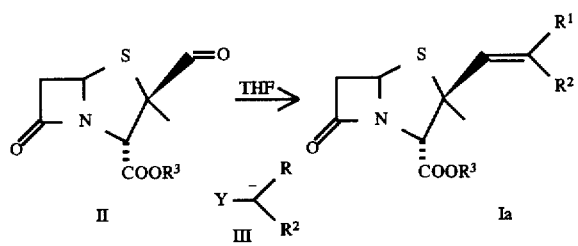

The substituents $R^1$, $R^2$ and $R^3$ are as defined above.

The aldehyde of formula II is converted into the alkenyl-substituted penams of formula Ia by direct reaction with an alkylidene-triphenylphosphorane (III; $Y=P^{\oplus(aryl)}_3$, Wittig reaction) or with an alkylphosphonate (III, $Y=(alkylO)_2PO$, Horner reaction) in the presence of an activating agent, for example, a base such as tri-ethylamine, sodium methylate, lithium diisopropylamine or DBU (1,5-diaza-bicyclo[4.3.0]non-5-ene). Suitable solvents are, for example, tetrahydrofuran, toluene, dichloromethane, acetonitrile or benzene. The reaction temperature can vary between –30° and 80° C. depending on the solvent which is used.

If desired, the compounds of formula I can also be made by reacting correspondingly substituted triphenylphosphonium halides with 1,2-butylene oxide as the base and solvent. In this case the preferred reaction temperature lies between 50° and 70° C. Compounds of formula I in which n signifies 0 are obtained.

The Peterson olefination and the Reformatsky synthesis are further possibilities for carrying out process variant a). In the case of the Peterson olefination, lithium derivatives of trialkylsilanes are reacted with compounds of formula II in the presence of a base. Scheme 2 shows the reaction with a lithium trimethylsilane of formula IV in which $R^1$ and $R^3$ are as defined above.

Scheme 2

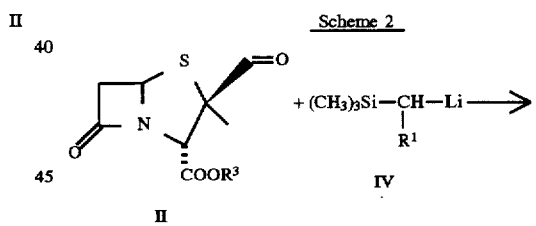

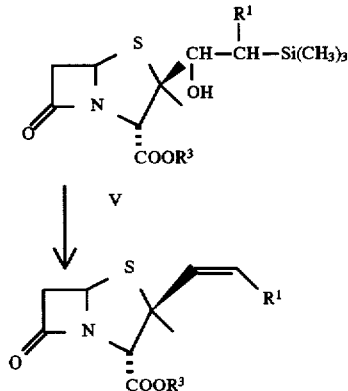

The 3β-alkenyl-penam derivatives of formula Ib result from the compounds of formula V by spontaneous dehydration. Compounds of formula I in which n signifies 0 and $R^2$ signifies hydrogen are obtained. In the case of the Reformatsky synthesis, compounds of formula II are condensed with organo-zinc derivatives of α-halo esters to the corresponding β-hydroxyl esters of formula VI, from which compounds of formula I in which n signifies 0, $R^1$ signifies $COR^4$, $R^4$ signifies lower alkyl and $R^2$ signifies hydrogen result by water cleavage, corresponding to Scheme 3.

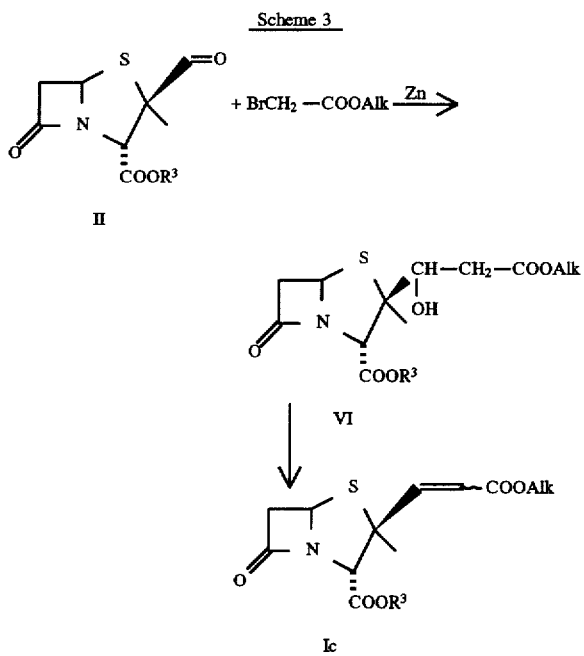

$R^3$ is as defined above.

The oxidation of the sulfide group to the sulfoxide group or sulfone group is effected according to methods known in the art. Reaction of the compounds of formula I in which n signifies 0 in a two-phase system with ruthenium tetroxide or with an aqueous potassium permanganate solution and with a hydrogen peroxide solution has been found to be especially suitable.

Other oxidation reagents such as $Na_2WO_4$ or peracids can also be used for the preparation of the penam sulfones. Di-chloromethane is an especially suitable solvent.

The compound of formula I in which n signifies 0 is conveniently dissolved in dichloromethane and added to an aqueous suspension consisting of sodium (meta)periodate, sodium bicarbonate and ruthenium(IV) oxide. After completion of the reaction the organic phase is separated, purified and dried.

Whether a sulfoxide or a sulfone results from this oxidation depends on the nature and/or amount of oxidation agent.

The conversion of a compound of formula I in which $R^3$ is different from hydrogen into a free acid and the conversion of a free acid into a pharmaceutically acceptable salt can be effected according to methods known in the art, in certain circumstances in a single procedure.

Ester groups, for example, benzyl, p-nitrobenzyl, benzhydryl, p-methoxybenzyl or allyl, can be cleaved off as follows:

Benzyl and p-nitrobenzyl by hydrogenation over palladium-carbon at about 0° C. to 80° C. in an organic solvent such as ethyl acetate, methanol- or water or by hydrolysis in the presence of sodium sulfide at about 0° C. to room temperature in a solvent such as e.g. DMF.

Allyl by palladium-(0)-catalyzed transallylation in the presence of a sodium or potassium salt of 2-ethylcaproic acid, benzhydryl with m-cresol at about 50° C. within 4–5 hours.

The compounds of formula II which are used as starting materials can be prepared from corresponding alcohols in analogy to the process described in Tetrahedron 43, No. 5, pp 1003–1012.

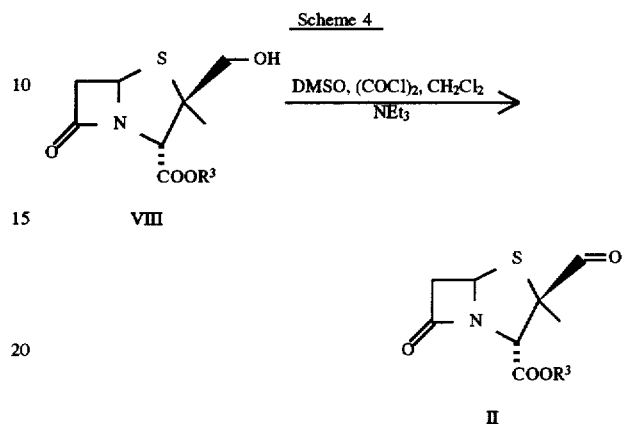

In this, $R^3$ is as defined above.

Reaction with oxalyl chloride in dichloromethane has been found to be of advantage, with the following procedure conveniently being used: dichloromethane and the oxidation agent are cooled to about −60° C., treated with DMSO and a compound of formula VIII and, after a reaction period of about 3 hours and addition of triethylamine, the cooling bath is removed. The thus-obtained aldehyde of formula II can be purified using usual methods.

Compounds of formula II are obtained analogously by oxidation with PCC (pyridine chlorochromate), Dess-Martin reagent, $MnO_2$ and the like.

As mentioned earlier, the compounds of formula I in accordance with the invention and pharmaceutically compatible salts thereof with bases exhibit pronounced β-lactamase-inhibiting activities against β-lactamases from various bacterial strains. As illustrated hereinafter, these therapeutically valuable properties can be determined in vitro on isolated β-lactamases.

A. Isolation of the β-lactamases

Various β-lactamases can be isolated from penicillin- or cephalosporin-resistant bacterial strains such as *Klebsiella pneumonia* NCTC 418, *Proteus vulgaris* 1028, *Bacillus licheniformis* 749/C, *Escherichia coli* SN01 and *Citrobacter freundii* 1203. For this purpose, the corresponding strains are cultivated in Tryptic Soy Broth (Difco) and harvested by centrifugation in the last logarithmic growth phase (when necessary 50–100 mg/l of ampicillin are added to the medium towards the end of the log-phase in order to induce the β-lactamase). The thus-obtained bacterial mass is treated with 20 mM Tris-HCl buffer (pH 7.0); the cells are broken open with a French press while cooling. The mixture is centrifuged (20,000 r/min.) for 20–30 minutes and a clear crude extract is obtained. The purification of the proteins is effected according to the methods of Cartwright, S. J. & Waley, S. G. [Blochem. J. 221, 505–512 (1980)]and, for *B. licheniformis*, Ellerby, L. M. et al. [Biochemistry 29, 5797–5806 (1990)].

B. Determination of the β-lactamase Activity

The determination of the activity of the isolated β-lactamases can be carried out according to the method of O'-Callaghan, C. H. et al. [Antimicr. Ag. Chemother. 1, 283–288 (1972)] using the chromogenic cephalosporin nitrocefin (87/312 from Glaxo). The requisite test batch contains per ml of water: 50 mM phosphate buffer (pH 7.0), 0.1 mM nitrocefin and sufficient enzyme (β-lactamase) to achieve a ΔA/min. of about 0.1. The cleavage of the substrate, which is accompanied by a change in color, is effected at 37° C. and is followed quantitatively at 482 nm using a spectral photometer.

C. Determination of the β-lactamase-Inhibiting Activity of the Compounds of Formula I The above-described cleavage of the chromogenic substrate by β-lactamases (test B) can be inhibited by the addition of compounds of formula I (inhibitors). Since it has been found that the inhibitors irreversibly inactivate the β-lactamase in a time-dependent reaction, the reaction (cleavage of the substrate) is in each case started by addition of the substrate after a pre-incubation period of β-lactamase with inhibitor of 15 minutes. As a measurement for the affinity of the particular tested inhibitor to the β-lactamase, which is a measurement of the strength of the inhibitor, there serves that concentration which inhibits by 50% (IC 50 in nM) the cleavage of the substrate (nitrocefin) effected under the above test conditions (test B) in the absence of an inhibitor. 4 to 6 tests with different concentrations of inhibitor were carried out in order to determine the $IC_{50}$. The determination of the $IC_{50}$ was effected by means of a graph.

The results obtained in the above test (test C) are presented in Tables 1 to 3 hereinafter.

TABLE 1

The $IC_{50}$ value, given in nM, is a measurement of the β-lactamase inhibition. An $IC_{50}$ value of 5 μM or less is considered to be significant.

β-Lactamase inhibiting activity of compounds of formula I

| Examples of compound of formula I with reference | $IC_{50}$ [μM] C. freundii 1982 | $IC_{50}$ [μM] E. coli CF 102 |
|---|---|---|
| Tazobactam (reference) | 0.900 | 0.015 |
| 6c (cis amide) | 4.340 | 0.130 |
| 6c (trans amide) | 2.250 | 0.054 |
| 5c (trans nitrile) | 0.696 | 0.681 |
| 5c (cis nitrile) | 0.210 | 0.126 |
| 2c (trans ethyl ester) | 0.370 | 0.456 |
| 4c (trans benzyl ester) | 0.478 | 0.444 |
| 8c (cis-chloro) | 0.590 | 0.055 |
| 9c (trans COCH₃) | 0.147 | 0.417 |
| 11c (trans 1,2,4-oxadiazol-3-yl) | 0.490 | 0.217 |
| 12c (trans 2-thiazolyl) | 0.410 | 0.054 |
| 12c (cis 2-thiazolyl) | 1.270 | 0.160 |
| 13c (trans 2-pyridinyl) | 1.010 | 0.092 |
| 14c (trans-CONMe(OMe)) | 2.490 | 0.181 |
| 15 (trans 2-pyridinylio) | 3.100 | 0.087 |
| 17b (trans CH=CH—CN(Z)) | 3.300 | 0.420 |
| 18c (gamma-lactam) | 14.250 | 0.320 |
| 20c (trans CH₂OH) | 6.92 | 0.590 |
| 22c (trans CH₂OCONH₂) | 0.479 | 0.763 |
| 23c (trans CH₂-pyridinium) | 15.700 | 0.142 |

TABLE 2

β-Lactamase inhibiting activity by combination of compounds of formula I with ceftriaxone
(1 part ceftriaxone + 4 parts inhibitor)

| Examples of compounds of formula I with reference | IC [μg/ml] C. freundii 1982 | IC [μg/ml] E. coli CF 102 |
|---|---|---|
| Ceftriaxone | 128 | 8 |
| Ceftriaxone + Tazobactam (reference) | 8 | 0.25 |
| Ceftriaxone + 6c (cis amide) | 4 | 0.12 |
| Ceftriaxone + 6c (trans amide) | NA | 0.12 |
| Ceftriaxone + 5c (trans nitrile) | 2 | 0.25 |
| Ceftriaxone + 5c (cis nitrile) | 1 | 0.25 |
| Ceftriaxone + 2c (trans ethyl ester) | 4 | 0.25 |
| Ceftriaxone + 4c (trans benzyl ester) | 16 | 2.00 |
| Ceftriaxone + 8c (cis chloro) | 4 | 0.25 |
| Ceftriaxone + 9c (trans COCH₃) | 1 | 0.25 |
| Ceftriaxone + 11c (trans 1,2,4-oxadiazol-3-yl) | 4 | 0.5 |
| Ceftriaxone + 12c (trans 2-thiazolyl) | 8 | 1 |
| Ceftriaxone + 12c (cis 2-thiazolyl) | 16 | 0.5 |
| Ceftriaxone + 13c (trans 2-pyridinyl) | 8 | 1 |
| Ceftriaxone + 14c (trans CONMe(OMe)) | 8 | 0.5 |
| Ceftriaxone + 15 (trans 2-pyridinylio) | 4 | 0.25 |
| Ceftriaxone + 17b (trans CH=CH—CN(Z)) | 8 | 0.5 |
| Ceftriaxone + 18c (gamma-lactam) | 16 | 1 |
| Ceftriaxone + 20c (trans-CH₂OH) | 8 | 0.5 |
| Ceftriaxone + 22c (trans CH₂OCONH₂) | 2 | 1 |
| Ceftriaxone + 23c (trans CH₂-pyridinium) | 8 | 0.25 |

MIC signifies minimum inhibitory concentration.

TABLE 3

In vitro activity of combinations of Example 5c with selected antibiotics against β-lactamase over-producer strains
(constant inhibitor concentration: 4 mg/l)

| | MIC E. cloacae | MIC C. freundii | MIC Ps. aeruginosa | MIC E. coli |
|---|---|---|---|---|
| Ceftriaxone | >64 | 64 | >64 | 16 |
| Ceftriaxone + 5c (cis nitrile) | 4 | 2 | 16 | ≦0.12 |
| Ceftriaxone + tazobactam | 64 | 32 | >64 | ≦0.12 |
| Ceftazidime | >64 | >64 | 32 | 32.00 |
| Ceftazidime + 5c (cis nitrile) | 4 | 8 | 2 | 0.5 |
| Ceftazidime + tazobactam | 64 | 64 | 8 | 0.5 |
| Piperacillin | >128 | >128 | >64 | >64 |
| Piperacillin + 5c (cis nitrile) | 8 | 8 | 16 | 4 |
| Piperacillin + tazobactam | 128 | 64 | 64 | 4 |
| Apalcillin | >128 | >128 | 64 | >64 |
| Apalcillin + 5c (cis nitrile) | 16 | 8 | 4 | 2 |
| Apalcillin + tazobactam | >128 | 64 | NA | 2 |

The products in accordance with the invention can be used as medicaments, for example, in the form of pharmaceutical preparations which contain them or their salts in admixture with a pharmaceutical, organic or inorganic inert carrier material which is suitable for parenteral or enteral administration, such as, for example, water, gelatin, gum arabic, lactose, starch, magnesium stearate, talc, vegetable oils, polyalkylene glycols, Vaseline, etc. The pharmaceutical preparations can be present unit dosage forms such as, for example, in solid form, for example, as tablets, dragées, suppositories, hard or soft gelatin capsules; or in liquid form, for example, as solutions, suspensions or emulsions. They may be sterilized and/or may contain adjuvants such as preserving, stabilizing, wetting or emulsifying agents, salts for varying the osmotic pressure, anesthetics or buffers. The compounds of formula I and their salts preferably come into consideration for parenteral administration and, for this purpose, are preferably prepared as lyophilizates or dry powders for dilution with usual agents such as water or isotonic saline.

As mentioned earlier, the compounds of formula I and their pharmaceutically compatible salts can be used in accordance with the invention in the control or prevention of illnesses, in human and non-human hosts, especially in the control of β-lactamase-forming pathogens in combination with β-lactam antibiotics, that is, antibiotics which contain a β-lactam ring, for example penicillins such as piperacillin, mezlocillin, azlocillin, apalcillin, benzyl-penicillin, phenoxymethylpenicillin, carbenicillin, methicillin, propicillin, tricarcillin, ampicillin, amoxicillin, mecillinam, aspoxicillin, azidocillin, bacampicillin, carfecillin sodium, carindacillin, clometocillin, cloxacillin, cyclacillin, dicloxacillin, diphenicillin sodium, epicillin, fenbencillin, floxacillin, hetacillin, lenampicillin, metampicillin, nafcillin sodium, oxacillin, penamecillin, penethamate hydriodid, penicillin G benethamine, penicillin G benzathine, penicillin benzhydrylamine, penicillin G calcium, penicillin G hydrabamine, penicillin G potassium, penicillin G procaine, penicillin N, penicillin O, penimepicycline, phenethicillin potassium, pivampicillin, quinacillin, sulbenicillin, talampicillin, temocillin, and ticarcillin, and cephalosporins such as ceftriaxone, ceftazidime, cefetamet, cefatamet pivoxil, cefotaxime, cefmenoxime, ceftizoxime, cefuroxime, cephaloridine, cephalotin, cefazolin, cephalexin, cefoxitin, cephacetrile, cefamandole, cephapirin, cephradine, cephaloglycine, cefpirome, cefepime, cefaclor, cefadroxil, cefatrizine, cefazedone, cefixime, cefodizime, cefonicid, cefoperazone, ceforanide, cefotiam, cefpimizole, cefpiramide, cefpodoxime proxetil, cefroxadine, cefsulodin, cefteram, ceftezole, ceftibuten, cefuzonam, cephalosporin C, and pivcefalexin, as well as penams like those found in S. McCombie et al., "Synthesis and In Vitro Activity of the Penem Antibiotics", 8 *Medicinal Research Reviews* 393 (1988), and carbapenems, such as imipenem ((5R,6S)-3-[[2-(Formimidoylamino)ethyl]thio]-6-[(R)-1-hydroxyethyl]-7-oxo-1-azabicyclo[3.2.0]hept-2-ene-2-carboxylic acid monohydrate), meropenem ((4R,5S,6S)-3-[(3S,5S)-5-Dimethylcarbamoylpyrrolidin-3-ylthio]-6-[(R)-1-hydroxyethyl]-4-methyl-7-oxo-1-azabicyclo[3.2.0]hept-2-ene-2-carboxylic acid), or like those found in R. Wise, "In Vitro and Pharmacokinetic Properties of the Carbapenems", 30 *Antimicrobial Agents and Chemotherapy* 343 (1986). Thereby, the compounds of formula I or pharmaceutically compatible salts thereof with bases can be administered before, simultaneously with or after the administration or intake of β-lactam antibiotics. Where the products in accordance with the invention are administered simultaneously with a β-lactam antibiotic, then this can be effected by administration as an ad-hoc combination or in the form of a pharmaceutical combination which contains a compound of formula I or a pharmaceutically compatible salt thereof with a base and a β-lactam antibiotic; such pharmaceutical combinations are also an object of the present invention.

The dosage of the compounds of formula I and of the pharmaceutically compatible salts thereof with bases can vary within wide limits and will, of course, be fitted in each particular case to the individual requirements and to the β-lactamase-producing pathogen to be controlled. In general, a daily dosage of about 0.1 to about 2.0 g should be appropriate. The ratio of β-lactamase inhibitor (compound of formula I or pharmaceutically compatible salt thereof with a base) to β-lactam antibiotic can also vary within wide limits and will be fitted to the individual requirements in each particular case. In general, a ratio of about 1:20 to about 1:1 should be appropriate.

As mentioned earlier, medicaments containing a compound of formula I or a pharmaceutically compatible salt thereof are also an object of the present invention, as is a process for the making of such medicaments which comprises bringing one or more compounds of formula I or pharmaceutically compatible salts thereof and, if desired, one or more other therapeutically valuable substances into a galenical administration form; in this connection reference is again made to the pharmaceutical combinations referred to above, which are also an object of the present invention. In particular, pharmaceutical combinations containing a compound of formula I or a pharmaceutically compatible salt thereof and a β-lactam antibiotic, for example, a penicillin such as piperacillin, mezlocillin, azlocillin, apalcillin, benzylpenicillin, phenoxymethyl-penicillin, carbenicillin, methicillin, propicillin, tricarcillin, ampicillin, amoxicillin, mecillinam, aspoxicillin, azidocillin, bacampicillin, carfecillin sodium, carindacillin, clometocillin, cloxacillin, cyclacillin, dicloxacillin, diphenicillin sodium, epicillin, fenbencillin, floxacillin, hetacillin, lenampicillin, metampicillin, nafcillin sodium, oxacillin, penamecillin, penethamate hydriodid, penicillin G benethamine, penicillin G benzathine, penicillin benzhydrylamine, penicillin G calcium, penicillin G hydrabamine, penicillin G potassium, penicillin G procaine, penicillin N, penicillin O, penimepicycline, phenethicillin potassium, pivampicillin, quinacillin, sulbenicillin, talampicillin, temocillin, and ticarcillin, a cephalosporin such as ceftriaxone, ceftazidime, cefetamet, cefatamet pivoxil, cefotaxime, cefmenoxime, ceftizoxime, cefuroxime, cephaloridine, cephalotin, cefazolin, cephalexin, cefoxitin, cephacetrile, cefamandole, cephapirin, cephradine, cephaloglycine, cefpirome, cefepime, cefaclor, cefadroxil, cefatrizine, cefazedone, cefixime, cefodizime, cefonicid, cefoperazone, ceforanide, cefotiam, cefpimizole, cefpiramide, cefpodoxime proxetil, cefroxadine, cefsulodin, cefteram, ceftezole, ceftibuten, cefuzonam, cephalosporin C, and pivcefalexin, or a penem, like those found in S. McCombie et al., "Synthesis and In Vitro Activity of the Penem Antibiotics", 8 *Medicinal Research Reviews* 393 (1988), or carbapenem, such as imipenem ((5R,6S)-3-[[2-(Formimidoylamino) ethyl]thio]-6-[(R)-1-hydroxyethyl]-7-oxo-1-azabicyclo[3.2.0]hept-2-ene-2-carboxylic acid monohydrate), meropenem ((4R,5S, 6S)-3-[(3S,5S)-5-Dimethylcarbamoylpyrrolidin-3-ylthio]-6-[(R)-1-hydroxyethyl]-4-methyl-7-oxo-1-azabicyclo [3.2.0]hept-2-ene-2-carboxylic acid) or like those found in R. Wise, "In Vitro and Pharmacokinetic Properties of the Carbapenems", 30 *Antimicrobial Agents and Chemotherapy* 343 (1986), are an object of the present invention. Such combinations are suitable for the control of β-lactamase-forming pathogens.

The following Examples are intended to illustrate the present invention in more detail, but are not intended to limit its scope in any manner. Unless otherwise stated, the Examples were conducted as follows.

EXAMPLE 1

Benzhydryl (2S,3R,5R)-3-formyl-3-methyl-7-oxo-4-thia-1-aza-bicyclo[3.2.0]heptane-2-carboxylate 100 ml of dichloromethane were treated with 0.84 ml (9.6 mmol) of oxalyl chloride under argon and cooled to −60° C. Thereto there were added dropwise 0.73 ml (10.25 mmol) of DMSO, followed by 2.5 g (6.52 mmol) of benzhydryl (2S,3R,5R)-3-hydroxymethyl-3-methyl-7-oxo-4-thia-1-aza-bicyclo[3.2.0]heptane-2-carboxylate dissolved in 100 ml of dichloromethane. The mixture was stirred at the same temperature for 3 hours and then 3.2 ml (23.0 mmol) of triethylamine were added. The cooling bath was removed and the mixture was left to warm to room temperature. The orange solution was poured into 1000 ml of 0.2N hydrochloric acid and the aqueous phase was extracted twice with dichloromethane. The organic phases were washed with water and saturated, aqueous sodium chloride solution, dried over sodium sulfate, filtered and concentrated on a rotary evaporator. The thus-obtained product (2.50 g, 100%) can be processed without further purification or can be recrystallized from diethyl ether.

Yield: 2.00 g (80%) of white crystal powder; m.p. 111.8°–112.8° C.
IR(KBr): 2720, 1788, 1743, 1718 cm$^{-1}$
MS: (M-CH$_2$CO)339
$^1$H-NMR (250 MHz, CDCl$_3$): δ[ppm]=1.26(s,3H), 3.06(dd, 1H,J=16.2 Hz, 2 Hz, 6-H), 3.54(dd,1H,J=16.2 Hz, 4 Hz,6-H), 5.34(s,1H,2-H), 5.42(dd,1H,J=2 Hz, 4 Hz,5-H), 6.95(s,1H,CHPh$_2$), 7.30–7.38 (m,10H,Ph), 9.20(s,1H).

EXAMPLE 2

(a) Benzhydryl (E)-(2S,3S,5R)-3-(2-ethoxycarbonyl-vinyl)-3-methyl-7-oxo-4-thia-1-aza-bicyclo[3.2.0]heptane-2-carboxylate 500 mg (1.30 mmol) of benzhydryl (2S,3R,5R)-3-formyl-3-methyl-7-oxo-4-thia-1-aza-bicyclo[3.2.0]heptane-2-carboxylate were dissolved in 20 ml of THF under argon and treated with 500 mg (1.40 mmol) of ethoxycarbonylmethylene-triphenylphosphorane. The yellow solution was stirred at 50° C. for 75 minutes and subsequently concentrated. The residue remaining behind was chromatographed over silica gel (0.040–0.063 mm particle size) with ethyl acetate:hexane (9:16) as the eluent.
Yield: 520 mg (88%) of yellow-orange resin;
IR (film): 1783, 1747, 1717, 1650 cm$^{-1}$
MS: (M-CONH) 406, (M-CHPh$_2$) 284
$^1$H-NMR (250 MHz, CDCl$_3$): δ[ppm]=1.31(t,3H,J=7 Hz) ,1.34(s,3H), 3.13(dd,1H,J=2 Hz, 16 Hz,6-H), 3.57(dd,1H, J=4 Hz, 16 Hz,6-H), 4.22(q,2H,J=7 Hz), 4.78(s,1H,2-H), 5.30(dd,1H,J=4.2 Hz, 5-H),
5.97(d,1H,J=15 Hz,=CH), 6.94(s,1H,CHPh$_2$), 7.07(d,1H, J=15 Hz,=CH), 7.30–7.38(m,10H,Ph).

(b) Benzhydryl (E)-(2S,3S,5R)-3-(2-ethoxycarbonyl-vinyl)-3-methyl-4,4,7-trioxo-4-thia-1-aza-bicyclo[3.2.0]heptane-2-carboxylate 250 mg (0.55 mmol) of benzhydryl (E)-(2S,3S,5R)-3-(2-ethoxy-carbonyl-vinyl)-3-methyl-7-oxo-4-thia-1-aza-bicyclo[3.2.0]-heptane-2-carboxylate were dissolved in 10 ml of dichloromethane and treated with 6.5 ml of glacial acetic acid. 260 mg (1.66 mmol) of potassium permanganate in 25 ml of water were added dropwise to the yellow solution. After completion of the addition stirring was continued for a further 30 minutes and then the brown reaction is mixture was treated with a 30% hydrogen peroxide solution until a colorless two-phase mixture forms. The phases were separated in a separating funnel and the aqueous phase was extracted twice with dichloromethane. The organic phase was washed with water, saturated sodium hydrogen carbonate solution and saturated sodium chloride solution, dried over sodium sulfate, filtered and concentrated. The residual oil was chromatographed over silica gel (particle size 0.040–0.063 mm) with ethyl acetate:hexane (9:16) as the eluent.
Yield: 170 mg (60%) of colorless foam.
IR(KBr): 1802, 1757, 1721, 1653, 1331, 960 cm$^{-1}$
MS: (M-H) 482.4
$^1$H-NMR (250 MHz, CDCl$_3$): δ[ppm]=1.26(s,3H), 1.35(t, 3H,J=7 Hz), 3.44–3.59(pseudo-m, 2H, 6-H), 4.29(q,2H, J=7 Hz), 4.60(dd,1H, J=4 Hz, 2 Hz,5-H), 4.61(s,1H,2-H), 5.99(d,1H,J=16 Hz,=CH), 6.94(s,1H, CHPh$_2$), 7.07(d, 1H,J=16 Hz,=CH), 7.23–7.40(m,10H,Ph).

(c) Sodium (E)-(2S,3S,5R)-3-(2-ethoxycarbonyl-vinyl)- 3-methyl-4,4,7-trioxo-4-thia-1-aza-bicyclo [3.2. 0]heptane-2-carboxylate 170 mg (0.35 mmol) of benzhydryl (E)-(2S,3S,5R)-3-(2-ethoxy-carbonyl-vinyl)-3-methyl-4,4,7-trioxo-4-thia-1-aza-bicyclo-[3.2.0]heptane-2-carboxylate were dissolved in 3 ml of m-cresol under argon and stirred at 50° C. for 4.5 hours. Thereafter, the mixture was treated with 12.5 ml of isobutyl methyl ketone and the yellow-orange solution was extracted three times with 3 ml of saturated, aqueous sodium hydrogen carbonate solution each time. The aqueous phase was washed twice with 5 ml of isobutyl methyl ketone each time, filtered over a fluted filter and subsequently adjusted to pH=1 with concentrated hydrochloric acid. The mixture was extracted with ethyl acetate, the organic phase was washed with saturated, aqueous sodium chloride solution, dried over sodium sulfate, filtered and concentrated on a rotary evaporator. The residual yellow resin was dissolved in 0.5 ml of ethyl acetate and treated with 108 µl of sodium 2-ethylcaproate (2N solution in ethyl acetate). The mixture was concentrated, the residue was treated with 1.5 ml of water and extracted once with n-hexane. Subsequently, the aqueous phase was chromatographed over polymeric hydrophobic gel with water as the eluent. The fractions containing the product were combined and lyophilized.
Yield: 60 mg (50%) of colorless lyophilizate
IR(KBr): 1782, 1715, 1627, 1396, 1192 cm$^{-1}$
MS: (M-Na)$^-$ 316.1
$^1$H-NMR (250 MHz, D$_2$O): δ[ppm]=1.31(t,3H,J=7 Hz), 1.66(s,3H), 3.46(dd,1H,J=16 Hz, 2 Hz,6-H), 3.71(dd,1H, J=16 Hz, 4 Hz,6-H), 4.28(q,2H,J=7 Hz), 4.62(s,1H,2-H), 5.15(dd,1H,J=2 Hz,4 Hz,5-H), 6.35(d,1H,J=16 Hz,=CH), 7.10(d,1H,J=16 Hz,=CH).

EXAMPLE 3

(a) Benzhydryl (E)-(2S,3S,5R)-3-(2-methoxycarbonyl-vinyl)-3-methyl-7-oxo-4-thia-1-aza-bicyclo[3.2.0]heptane-2-carboxylate 200 mg (0.52 mmol) of benzhydryl (2S,3R,5R)-3-formyl-3-methyl-7-oxo-4-thia-1-aza-bicyclo[3.2.0]heptane-2-carboxylate were converted into benzhydryl (E)-(2S,3S,5R) -3-(2-methoxycarbonyl-vinyl)-3-methyl-7-oxo-4-thia-1- aza-bicyclo[3.2.0]heptane-2carboxylate by reaction with 193 mg (0.58 mmol) of methoxycarbonylmethylene-triphenylphorsphorane according to Example 2.

Yield: 209 mg (91%) of colorless foam
IR (film): 1782, 1745, 1724, 1651 cm$^{-1}$
MS: (M+NH$_4^+$) 455.3

EXAMPLE 4

(a) Benzhydryl (E)-(2S,3S,5R)-3-(2-benzyloxycarbonyl-vinyl)-3-methyl-7-oxo-4-thia-1-aza-bicyclo[3.2.0]heptane-2-carboxylate 763 mg (2.0 mmol) of benzhydryl (2S,3R,5R)-3-formyl-3-methyl-7-oxo-4-thia-1-aza-bicyclo[3.2.0]heptane-2-carboxylate were dissolved in 15 ml of THF under argon, treated with 821 mg (2.0 mmol) of benzyloxycarbonylmethylene-triphenylphosphorane and the orange solution was stirred at 50° C. for 2 hours. It was left to cool to room temperature, the solvent was removed on a rotary evaporator and the red-brown oil was chromatographed over silica gel (particle size 0.040–0.063 mm) with ethyl acetate:hexane (9:16) as the eluent.

Yield: 800 mg (78%) of orange foam
IR (film): 1782, 1746, 1721, 1649, 985 cm$^{-1}$
MS: (M+H)+514.3
$^1$H-NMR (250 MHz, CDCl$_3$): δ[ppm]=1.33(s,3H), 3.11(dd, 1H,J=16 Hz, 1.6 Hz, 6-H), 3.56(dd,1H,J=16 Hz, 4.2 Hz, 6-H), 4.78(s,1H,2-H), 5.20(s,2H), 5.36(dd,1H, J=1.6 Hz, 4.2 Hz, 5-H), 6.01(d,1H,J=15 Hz,=CH), 6.93(s,1H, CHPh$_2$), 7.12(d,1H,J=15 Hz, =CH), 7.30–7.43(m,15H, Ph).

(b) Benzhydryl (E)-(2S,3S,5R)-3-(2-benzyloxycarbonyl-vinyl)-3-methyl-4,4,7-trioxo-4-thia-1-aza-bicyclo[3.2.0]heptane-2-carboxylate 800 mg (1.56 mmol) of benzhydryl (E)-(2S,3S,5R)-3-(2-benzyl-oxycarbonyl-vinyl)-3-methyl-7-oxo-4-thia-1-aza-bicyclo[3.2.0]-heptane-2-carboxylate were oxidized according to Example 2.

Yield: 255 mg (30%) of colorless foam
IR(KBr): 1802, 1757, 1723, 1650, 1332 cm$^{-1}$
MS: (M-H)$^-$ 544.2
$^1$H-NMR (250 MHz, CDCl$_3$): δ[ppm]=1.25(s,3H), 3.47(dd, 1H,J=16 Hz, 2 Hz,6-H), 3.55(dd,1H,J=16 Hz, 4 Hz, 6-H), 4.66(dd,1H,J=2 Hz, 4 Hz, 5-H),4.81(s,1H,2-H), 5.26(s, 2H), 6.02(d,1H,J=16 Hz,=CH), 6.93(s,1H, CHPh$_2$), 7.22 (d,1H,J=16 Hz,=CH), 7.13–7.14(m,15H,Ph).

(c) Sodium (E)-(2S,3S,5R)-3-(2-benzyloxycarbonyl-vinyl)-3-methyl-4,4,7-trioxo-4-thia-1-aza-bicyclo[3.2.0]heptane-2-carboxylate 250 mg (0.46 mmol) of benzhydryl (E)-(2S,3S,5R)-3-(2-benzyl-oxycarbonyl-vinyl)-3-methyl-4,4,7-trioxo-4-thia-1-aza-bicyclo[3.2.0]heptane-2-carboxylate were deprotected according to Example 2.

Yield: 54 mg (30%) of beige lyophilizate
IR (KBr): 1781, 1719, 1626, 1322, 1189, 979 cm$^{-1}$
MS: (M-H)$^-$ 378.2
$^1$H-NMR (250 MHz, D$_2$O): δ[ppm]=1.65(s,3H), 3.45(dd, 1H,J=17 Hz, 2 Hz,6-H), 3.71(dd,1H,J=17 Hz, 4 Hz,6-H), 4.63(s,1H,2-H), 5.14 (dd,1H,J=4 Hz, 2 Hz,5-H), 5.29(s, 2H), 6.42(d,1H,J=16 Hz,=CH), 7.13(d,1H,J=16 Hz,=CH), 7.42–7.55(m,5H,Ph).

EXAMPLE 5

(a) Benzhydryl (E/Z)-(2S,3S,5R)-3-(2-cyanoethenyl)-3-methyl-7-oxo-4-thia-1-aza-bicyclo[3.2.0]heptane-2-carboxylate Method A:

1.0 g (2.62 mmol) of benzhydryl (2S,3R,5R)-3-formyl-3-methyl-7-oxo-4-thia-1-aza-bicyclo[3.2.0]heptane-2-carboxylate and 30 ml of toluene were added to 946 mg (3.14 mmol) of cyanoethylene-triphenylphosphorane under argon. The brown suspension was stirred for 1 hour, concentrated and chromatographed over silica gel (particle size 0.040–0.063 mm) with ethyl acetate:n-hexane (3:1) as the eluent.

Yield: 1.0 g (94%) of isomer mixture, E:Z 3:1
Spectroscopic data of the mixture:
IR (film): 2224, 1781, 1744 cm$^{-1}$
MS: (M+Na$^+$) 427.2
$^1$H-NMR (250 MHz, CDCl$_3$)(E isomer): δ[ppm]=1.32(s, 3H), 3.13(dd,1H,J=16 Hz, 1.6 Hz, 6-H), 3.63(dd,1H,J=16 Hz, 4.4 Hz,6-H), 4.74(s,1H,2-H), 5.41(dd,1H,J=4.4 Hz, 1.6 Hz,5-H), 5.54(d,1H,J=15 Hz =CH), 6.82(d,1H,J=15 Hz,=CH), 6.95(s,1H,CHPh$_2$), 7.30–7.44(m,10H, Ph).
1H-NMR (250 MHz, CDCl$_3$) (Z isomer): δ[ppm]=1.61(s, 3H), 3.18(dd,1H,J=16 Hz,1.5 Hz,6-H), 3.64(dd,1H,J=16 Hz, 4.6 Hz,6-H), 4.86(s,1H,2-H), 5.41(d,1H,J=12 Hz,=CH), 5.44(dd,1H,J=1.5 Hz, 4.6 Hz,5-H), 6.63(d,1H, J=12 Hz,=CH), 6.95(s,1H,CHPh$_2$), 7.30–7.44(m,10H, Ph).

Method B:

A suspension of 2.88 g (9.56 mmol) of cyanomethylene-tri-phenylphosphorane in 24 ml of lithium perchlorate solution (0.4M in acetonitrile) was cooled to −20° C. under argon. A solution of 3.32 g (8.70 mmol) of benzhydryl (2S,3R,5R)-3-formyl-3-methyl-7-oxo-4-thia-1-aza-bicyclo [3.2.0]heptane-2-carboxylate in 30 ml of acetonitrile was added dropwise thereto, the mixture was stirred at the same temperature for 4 hours and the solvent was removed on a rotary evaporator. The residue remaining behind was taken up in 100 ml of ethyl acetate, extracted three times with water and once with saturated sodium chloride solution, dried over magnesium sulfate, filtered and concentrated. The residual oil was purified over silica gel (particle size 0.040–0.063 mm) with methylene chloride as the eluent.

Yield: 3.34 g (94%) of isomer mixture, E:Z 1:4

(b) Benzhydryl (E/Z)-(2S,3S,5R)-3-(2-cyanoethenyl)-3-methyl- 4,4,7-trioxo-4-thia-1-aza-bicyclo[3.2.0]heptane-2-carboxylate Benzhydryl (E/Z)-(2S,3S,5R)-3-(2-cyanoethenyl)-3-methyl-4,4,7-trioxo-4-thia-1-aza-bicyclo[3.2.0]heptane-2-carboxylate was prepared in the same manner as described in Example 2 by oxidizing benzhydryl (E/Z)-(2S,3S,5R)-3-(2-cyanoethenyl)-3-methyl-7-oxo-4-thia-1-aza-bicyclo [3.2.0]heptane-2-carboxylate. The two isomers can be separated by chromatography over silica gel (particle size 0.040–0.063 mm) with ethyl acetate:n-hexane (9:16). The Z isomer was eluted as the first component.

Yield:
Z: 76 mg (7%) of colorless oil
E: 253 mg (23%) of colorless foam
Spectroscopic data E isomer:
MS: (M+NH$_4$)$^+$ 454.2
IR (KBr): 2228, 1802, 1758, 1334, 1192, 990 cm$^{-1}$
$^1$H-NMR (250 MHz, CDCl$_3$): δ[ppm]=1.24(s,3H), 3.50(dd, 1H,J=16 Hz, 2.2 Hz),6-H), 3.60(dd,1H,J=16 Hz, 4 Hz,6-

H), 4.65(dd,1H,J=2 Hz, 4 Hz,5-H, 4.75(s,1H,2-H), 5.37 (d,1H,J=16 Hz,=CH), 6.85(d,1H,J=16 Hz,=CH), 6.98 (S,1H,CHPh$_2$), 7.25–7.45(m,10H,Ph).

Spectroscopic data Z isomer:
MS: (M–H)$^-$ 435.3
IR (KBr): 2220, 1801, 1757, 1333, 1190 cm$^{-1}$
1H-NMR (250 MHz, CDCl$_3$): δ[ppm]=1.67(s, 3H), 3.48(dd, 1H, J=16 Hz, 2.4 Hz, 6-H), 3.64(dd, 1H, J=16 Hz, 4.6 Hz, 6-H), 4.72(dd, 1H, J=2.4 Hz, 4.6 Hz, 5-H), 4.85(s,1H, 3-H), 5.90(d,1H,J=12 Hz,=CH), 6.41(d,1H,J=12 Hz, =CH), 6.97(s,1H,CHPh$_2$), 7.26–7.44(m,10H,Ph).

(c) Sodium (E)-(2S,3S,5R)-3-(2-cyanoethenyl)-3-methyl-4,4,7-trioxo-4-thia-1-aza-bicyclo[3.2.0]heptane-2carboxylate 215 mg (0.5 mmol) of benzhydryl (E)-(2S,3S,5R)-3-(2-cyano-ethenyl)-3-methyl-4,4,7-trioxo-4-thia-1-aza-bicyclo [3.2.0]-heptane-2-carboxylate were deprotected according to Example 2.
Yield: 110 mg (82%) of white lyophilizate
IR (KBr): 2240, 1782, 1629, 1397, 1141 cm$^{-1}$
MS: (M–Na)$^-$ 269.0
$^1$H-NMR (250 MHz, CDCl$_3$): δ[ppm]=1.64(s,3H), 3.47 (dd,1H,J=16 Hz, 2 Hz,6-H), 3.72(dd,1H,J=16 Hz, 4 Hz,6-H), 4.62(s,1H,2-H), 5.15 (dd,1H,J=2 Hz,4 Hz,5-H), 6.07(d, 1H,J=16 Hz,=CH), 7.08(d,1H,J=16 Hz,=CH).

Sodium (Z)-(2S,3S,5R)-3-(2-cyanoethenyl)-3-methyl-4,4,7-trioxo-4-thia-1-aza-bicyclo[3.2.0]heptane-2-carboxylate 95 mg (0.2 mmol) of benzhydryl (Z)-(2S,3S,5R)-3-(2-cyanoethenyl)-3-methyl-4,4,7-trioxo-4-thia-1-aza-bicyclo [3.2.0]heptane-2-carboxylate were dissolved in 3 ml of m-cresol and stirred at 50° C. for 45 minutes. The reaction mixture was treated with 10 ml of isobutyl methyl ketone and 120 µl Of sodium 2-ethylcaproate (2N in ethyl acetate, 1.1 eq.). The mixture was extracted twice with 3 ml Of water each time, the combined aqueous phases are washed with 10 ml of isobutyl methyl ketone and lyophilized. The yellow lyophilizate was dissolved in 1.3 ml of water and chromatographed over polymeric hydrophobic gel.
Yield: 50 mg (80%) of colorless lyophilizate
IR (KBr): 2222, 1782, 1626, 1395, 1323, 1141 cm$^{-1}$
$^1$H-NMR (250 MHz, D$_2$O): δ[ppm]=1.94(s,3H), 3.47(dd, 1H,J=16 Hz, 1.6 Hz, 6-H), 3.73(dd, 1H, J=16 Hz, 4.4 Hz, 6-H), 4.80(s,1H,2-H), 5.19(dd, 1H, J=16 Hz, 4.4 Hz,5-H), 6.15(d,1H,J=12 Hz,=CH), 6.68 (d,1H,J=12 Hz,=CH).

EXAMPLE 6

(a) Benzhydryl (E/Z)-(2S,3S,5R)-3-(2-carbamoyl-vinyl)-3-methyl-7-oxo-4-thia-1-aza-bicyclo [3.2.0]heptane-2-carboxylate 2.60 g (6.86 mmol) of benzhydryl (2S,3R,5R)-3-formyl-3-methyl-7-oxo-4-thia-1-aza-bicyclo[3.2.0]heptane-2-carboxylate and 2.15 g (6.86 mmol) of carbamoylmethylene-triphenylphosphorane were suspended in 60 ml of THF under argon and stirred at 50° C. for 45 minutes. Insoluble material was filtered off under suction and the filtrate was concentrated on a rotary evaporator. The brown oil was chromatographed on silica gel (particle size 0.040–0.063 mm) with ethyl acetate:n-hexane (1:1) as the eluent and the two isomers are separated. TheZ isomer was eluted before the E isomer, both can be obtained as crystalline solids from CH$_2$Cl$_2$:n-hexane.

Z Isomer:
Yield: 217 mg (7.5%) of colorless solid
IR (KBr): 3441, 1777, 1743, 1678, 986 cm–1
MS: (M-CHPh$_2$) 255
M.p. (melting point): 188°–189° C.
1H-NMR (250 MHz, CDCl$_3$): δ[ppm]=1.58(s,3H), 3.11(dd, 1H,J=16 Hz, 1.60 Hz,6-H), 3.57(dd,1H,J=16 Hz, 4.40 Hz,6-H), 5.23(s,1H,2-H), 5.36(dd,1H,J=4.40 Hz, 1.60 Hz,5-H), 5.5(pseudo-d,2H,NH2), 5.75 (d,1H,J=12 Hz,=CH), 6.24(d,1H,J=12 Hz,=CH), 6.92(s,1H, CHPh$_2$), 7.29–7.43(m,10H, Ph).

E Isomer:
Yield: 347 mg (12%) of crystalline solid
IR (KBr): 3444, 1775, 1728, 1671 cm$^{-1}$
MS: (M+H)$^+$ 423.4
M.p.: 142° C.(dec.)
$^1$H-NMR (250 MHz, CDCl$_3$): δ=1.36(s,3H), 3.11(dd,1H, J=16 Hz, 2.0 Hz, 6H), 3.56(dd,1H,J=16 Hz, 4.2 Hz,6-H), 4.83(s,1H,2-H), 5.37(dd,1H,J=2.0 Hz, 4.2 Hz,5-H), 5.55(s, br,2H,NH2), 5.97(d,1H, J=15 Hz,=CH), 6.94(s,1H, CHPh$_2$), 6.95(d,1H,J=15 Hz,=CH), 7.28–7.40(m,10H,Ph).

(b) Benzhydryl (Z)-(2S,3S,5R)-3-(2-carbamoyl-vinyl)-3-methyl-4,4,7-trioxo-4-thia-1-aza-bicyclo [3.2.0]heptane-2-carboxylate 370 mg (0.875 mmol) of benzhydryl (Z)-(2S,3S,5R)-3-(2-carbamoyl-vinyl)-3-methyl-7-oxo-4-thia-1-aza-bicyclo [3.2.0]heptane-2carboxylate were oxidized in accordance with Example 2. A mixture of ethyl acetate:n-hexane (1:1) was used as the eluent.
Yield: 225 mg (57%) of colorless foam
IR (KBr): 1799, 1750, 1678, 1326, 1188, 1140 cm$^{-1}$
MS: (M+H)$^+$ 455.2
$^1$H-NMR (250 MHz, CDCl$_3$): δ[ppm]=1.50(s,3H), 3.45(dd, 1H,J=16 Hz, 2Hz,6-H), 3.56(dd,1H,J=16 Hz, 4 Hz,6-H), 4.67(dd,1H,J-4 Hz, 2 Hz,5-H), 5.28(s,1H,2-H), 5.63(s,br, 1H,NH$_2$), 5.84(d,1H,J=13 Hz,=CH), 6.69 (s,br,1H,NH$_2$), 6.39(d,1H,J=13 Hz,=CH), 6.93(s,1H,CHPh$_2$), 7.29–7.41 (m,10H,Ph).

Benzhydryl (E)-(2S,3S,5R)-3-(2-Carbamoyl-vinyl)-3-methyl-4,4,7-trioxo-4-thia-1-aza-bicyclo[3.2.0]heptane-2-carboxylate 0.64 g (1.51 mmol) of benzhydryl (E)-(2S,3R,5R)-3-(2-carbamoyl-vinyl)-3- methyl-7-oxo-4-thia-1-aza-bicyclo [3.2.0]heptane-2carboxylate were dissolved in 30 ml of methylene chloride and cooled to 0° C. 1.86 g (7.55 mmol) of meta-chloroperbenzoic acid (content: 70–75%, 5 eq.) in 30 ml of methylene chloride were added dropwise thereto, the cooling bath was removed after completion of the addition and the mixture was stirred at room temperature for 6 hours. The reaction solution was extracted with sodium sulfite solution (30% in saturated aqueous sodium bicarbonate solution) and washed with saturated aqueous sodium chloride solution. The solution was dried over magnesium sulfate, filtered, the solvent was removed on a rotary evaporator and the residue remaining behind was recrystallized using methylene chloride:n-hexane.
Yield: 210 mg (30%) of colorless solid
IR (KBr): 1799, 1756, 1686, 1329, 1143, 1191 cm$^{-1}$
MS: (M+H$^+$) 455.3
M.p.: 186°–188° C.
$^1$H-NMR (250 MHz, CDCl$_3$): δ[ppm]=1.30(s,3H), 3.47(dd, 1H,J=16 Hz, 3.0 Hz,6-H), 3.61(dd,1H,J=16 Hz, 4.4 Hz,6-H), 4.67(dd,1H,J=3.0 Hz, 4.4 Hz,5-H), 4.82(s,1H,2-H), 5.53(s,br,2H,NH2), 6.03(d,1H, J=16 Hz,=CH), 6.98(d, 1H,J=16 Hz,=CH), 6.94(s,1H,CHPh$_2$), 7.26–7.40(m, 10H,Ph).

(c) Sodium (Z)-(2S,3S,5R)-3-(2-carbamoyl-vinyl)-3-methyl-4,4,7-trioxo-4-thia-1-aza-bicyclo[3.2.0]heptane-2carboxylate 135 mg (0.30 mmol) of benzhydryl (Z)-(2S,3S,5R)-3-(2-carbamoyl-vinyl)-3-methyl-4,4,7-trioxo-4-thia-1-aza-bicyclo[3.2.0]heptane-2-carboxylate was deprotected according to Example 2.
Yield: 67 mg (70%) of colorless lyophilizate
IR (KBr): 3434, 1:781, 1668, 1626, 1397, 1317, 1139 cm$^{-1}$
MS: (M–Na)$^-$ 287.2
$^1$H-NMR (250 MHz, D$_2$O): δ[ppm]=1.76(s,3H), 3.44(dd, 1H,J=16 Hz, 1.2 Hz,6-H), 3.69(s,1H,J=16 Hz, 4 Hz,6-H), 4.68(s,1H,2-H), 5.10 (dd,1H,J=4 Hz, 1.2 Hz,5-H), 5.94 (d,1H,J=13 Hz,=CH), 6.53(d,1H, J=13 Hz,=CH).

Sodium (E)-(2S,3S,5R)-3-(2-carbamoyl-vinyl)-3-methyl-4,4,7-trioxo-4-thia-1-azabicyclo[3.2.0]heptane-2-carboxylate 350 mg (0.78 mmol) of benzhydryl (E)-(2S,3S,5R)-3-(2-carbamoyl-vinyl)-3-methyl-4,4,7-trioxo-4-thia-1-aza-bicyclo[3.2.0]heptane-2-carboxylate were deprotected according to Example 2.
Yield: 190 mg (80%)
IR (KBr): 1782, 1684, 1622, 1398, 1318, 1140 cm$^{-1}$
MS: (M–Na)$^-$ 287.1
$^1$H-NMR (250 MHz, D$_2$O): δ[ppm]=1.66(s,3H), 3.46(dd, 1H,J=17 Hz, 1.4 Hz, 6-H), 3.71(dd, 1H, J=17 Hz, 4.0 Hz,6-H), 4.62(s,1H,2-H), 5.14(dd,J=1.4 Hz, 4.0 Hz,5-H), 6.46(d,1H,J=16 Hz,=CH), 6.88(d,1H,J=16 Hz,=CH).

EXAMPLE 7

(a) Benzhydryl (E)-(2S,3S,5R)-3-(2-ethoxycarbonyl-propenyl)-3-methyl-7-oxo-4-thia-1-aza-bicyclo[3.2.0]heptane-2-carboxylate 286 mg (0.75 mmol) of benzhydryl (2S,3R,5R)-3-formyl-3-methyl-7-oxo-4-thia-1-aza-bicyclo[3.2.0]heptan-2-carboxylate were dissolved in 12 ml of THF under argon and treated with 271 mg (0.75 mmol) of (1-ethoxycarbonylethylidene)-triphenylphosphorane. The yellow solution was stirred at 70° C. for 6 hours and subsequently concentrated. The residue remaining behind was chromatographed over silica gel (0.040–0.063 mm particle size) with ethyl acetate:hexane (9:16) as the eluent.
Yield: 157 mg (45%) of pale yellow solid
IR (film): 1788, 1754, 1704, 1642 cm$^{-1}$
MS: (M+NH$_4^+$) 483.4
$^1$H-NMR (400 MHz, CDCl$_3$): δ[ppm]=1.32(t,3H,J=7.1Hz) ,1.38(s,3H), 2.03(d,3H,J=1.5 Hz), 3.05(dd,1H,J=1.8 Hz, 16 Hz,6-H), 3.57(dd,1H, J=4.3 Hz, 16 Hz,6-H), 4.23(q, 2H,J=7.1Hz), 4.89(s,1H,2-H), 5.29(dd, 1H,J=4.3, 1.8 Hz,5-H), 6.94(s,1H,CHPh$_2$), 7.20(d,1H,J=1.5 Hz,=CH), 7.30–7.36(m,10H,Ph).

EXAMPLE 8

(a) Benzhydryl (E,Z)-(2S,3S,5R)-3-(2-chloro-vinyl)-3-methyl-7-oxo-4-thia-1-aza-bicyclo[3.2.0]heptane-2-carboxylate A suspension of 1.37 g (4.40 mmol) of chloromethylene-triphenylphosphorane in 25 ml of diethyl ether was cooled to 0° C. and treated with 1.60 g (4.20 mmol) of benzhydryl (2S,3R,5R)-3-formyl-3-methyl-7-oxo-4-thia-1-aza-bicyclo[3.2.0]heptane-2carboxylate. The cooling bath was removed and the mixture was stirred at room temperature for a further 3 hours. The orange suspension was filtered and subsequently concentrated. The residue remaining behind was chromatographed over silica gel (0.040–0.063 mm particle size) with ethyl acetate:hexane (1:2) as the eluent.
Yield: 1.20 g (69%) of yellow isomer mixture, E:Z 7:9
Spectroscopic data of the mixture:
IR (film): 1782, 1747, 1590, 1496, 1251 cm$^{-1}$
MS: (M+NH$_4^+$) 413.

(b) Benzhydryl (E/Z)-(2S,3S,5R)-3-(2-chloro-vinyl)-3-methyl-4,4,7-trioxo-4-thia-1-aza-bicyclo[3.2.0]heptane-2-carboxylate 2.98g (14.05 mmol) of sodium metaperiodate were dissolved in 30 ml of water under argon and cooled to 0° C. The solution was treated with 0.93 g (11.17 mmol) of sodium bicarbonate followed by 45 ml of acetonitrile as well as 60 ml of methylene chloride. 9 mg (0.070 mmol) of ruthenium dioxide and subsequently the solution of 1.20 g (2.90 mmol) of benzhydryl (E/Z)-(2S,3S,5R)-3-(2-chloro-vinyl)-3-methyl-7-oxo-4-thia-1-aza-bicyclo[3.2.0]heptane-2-carboxylate were added to the two-phase mixture. The cooling bath was removed and the reaction mixture was stirred until the reaction has finished (tlc control). Subsequently, the mixture was treated with 2 g of active charcoal and 20 ml of saturated sodium chloride solution, stirred for 5 minutes and suction filtered over Dicalite. The phases were separated in a separating funnel, the aqueous phase was extracted twice with methylene chloride and the combined organic extracts were washed with water and saturated sodium chloride solution, dried over magnesium sulfate/fuller's earth, filtered and evaporated. The residual oil was chromatographed over silica gel (particle size 0.040–0.063 mm) with ethyl acetate:n-hexane (1:2) as the eluent, the two isomers being separated in this manner. The Z isomer was eluted as the first component.
Yield:
Z: 495 mg (38%) of colorless foam
E: 385 mg (30%) of colorless foam
Spectroscopic data E Isomer:
MS: (M+NH$_4$)$^+$ 463.4
IR (KBr): 1800, 1756, 1612, 1331, 1143, 700 cm$^{-1}$
Spectroscopic data Z Isomer:
MS: (M+NH$_4$)$^+$ 463.4
IR (KBr): 1800, 1755, 1630, 1330, 1143, 700 cm$^{-1}$ (c) Sodium (E)-(2S,3S,5R)-3-(2-chloro-vinyl)-3-methyl-4,4,7-trioxo-4-thia-1-aza-bicyclo[3.2.0]heptane-2-carboxylate 385 mg (0.86 mmol) of benzhydryl (E)-(2S,3S,5R)-3-(2-chloro-vinyl)-3-methyl-4,4,7-trioxo-4-thia-1-aza-bicyclo[3.2.0]heptane-2-carboxylate are dissolved in 2.3 ml of m-cresol under argon and stirred at 50° C. for 4 hours. Subsequently, the mixture was diluted with 15 ml of isobutyl methyl ketone, treated with 0.50 ml of sodium 2-ethylcaproate (2N solution in ethyl acetate) and extracted three times with 8 ml of water each time. The combined aqueous phases were washed once with 10 ml of isobutyl methyl ketone, lyophilized and the lyophilizate obtained was chromatographed over polymeric hydrophobic gel with water as the eluent.
Yield: 57 mg (32%)
MS: (M–Na)$^-$ 278.2
IR (KBr): 1780, 1626, 1564, 1417, 1329, 1145 cm$^{-1}$ Sodium (Z)-(2S,3S,5R)-3-(2-chloro-vinyl)-3-methyl-4,4,7-trioxo-4-thia-1-aza-bicyclo[3.2.0]heptane-2-carboxylate 400 mg (0.90 mmol) of benzhydryl (Z)-(2S,3S,5R)-3-(2-chloro-vinyl)-3-methyl-4,4,7-trioxo-4-thia-1-aza-bicyclo[3.2.0]heptane-2-carboxylate were deprotected according to Example 8.

Yield: 176 mg (65%) of colorless lyophilizate
MS: (M−Na)⁻ 278.2
IR (KBr): 1779, 1–626, 1398, 1321, 1142 cm⁻¹
Elementary analysis: C₉H₉ClNO₅SNa (301.676)

Calc. C 35.83 H 3.01 N 4.64
Found#) C 35.72 H 3.04 N 4.65

) anhydrous, calculated with 5.53 % water

EXAMPLE 9

(a) (E)-(2S, 3S,5R)-3-methyl-7-oxo-3-(3-oxo-but-1-enyl)-4-thia-1-aza-bicyclo[3.2.0]heptane-2-carboxylate 381 mg (1.00 mmol) of benzhydryl (2S,3R,5R)-3-formyl-3-methyl-7-oxo-4-thia-1-aza-bicyclo[3.2.0]heptane-2-carboxylate were dissolved in 12 ml of THF under argon and treated with 350 mg (1.10 mmol) of acetylmethylene-triphenylphosphorane. The mixture was stirred at 50° C. for 6 days and subsequently concentrated. The residue remaining behind was chromatographed over silica gel (0.040–0.063 mm particle size) with ethyl acetate:methylene chloride (95:5) as the eluent.
Yield: 221 mg (52%) of white resin
IR (film): 1782, 1681, 1627, 1319, 1141, 980 cm⁻¹
MS: (M−Na)⁻ 286.1

(b) Benzhydryl (E)-(2S,3S,5R)-3-methyl-3-(3-oxo-but-1-enyl)-4,4,7-trioxo-4-thia-1-aza-bicyclo[3.2.0]heptane-2carboxylate 221 mg (0.49 mmol) of benzhydryl (E)-(2S,3S,5R)-3-methyl-7-oxo-3-(3-oxo-but-1-enyl)-4-thia-1-aza-bicyclo[3.2.0]heptane-2carboxylate were oxidized according to Example 8. Chromatography is carried out once over silica gel (particle size 0.040–0.063 mm) with ethyl acetate:n-hexane (9:16) as the eluent and crystallization was carried out from methylene chloride/n-hexane.
Yield: 95 mg (40%) of colorless crystals
MS: (M+NH₄)⁺ 471.2
IR (KBr): 1798, 1760, 1682, 1627, 1330, 1193, 1142, 976 cm⁻¹
M.p.: 183°–184° C.

(c) Sodium (E)-(2S,3S,5R)-3-methyl-3-(3-oxo-but-1-enyl)-4,4,7-trioxo-4-thia-1-aza-bicyclo [3.2.0]heptane-2-carboxylate 250 mg (0.55 mmol) of benzhydryl (E)-(2S,3S,5R)-3-methyl-3-(3-oxo-but-1-enyl)-4,4,7-trioxo-4-thia-1-aza-bicyclo[3.2.0]heptane-2-carboxylate were deprotected according to Example 8.
Yield: 47 mg (27%) of colorless lyophilizate
MS: (M−Na)⁻ 286.1
IR (KBr): 1782, 1681, 1627, 1394, 1319, 1141, 980 cm⁻¹

EXAMPLE 10

(a) (E)-(2S, 3S,5R)-3-(2-Formyl-vinyl)-3-methyl-7-oxo-4-thia-1-aza-bicyclo [3,2, 0]heptane-2-carboxylate 3.81 g (10.0 mmol) of benzhydryl (2S,3R,5R)-3-formyl-3-methyl-7-oxo-4-thia-1-aza-bicyclo[3.2.0]heptane-2-carboxylate were dissolved in 40 ml of methylene chloride under argon and treated with 3.34 g (11.0 mmol) of formylmethylene-triphenylphosphorane. The yellow solution was stirred at room temperature for 3 days and subsequently concentrated. The residue remaining behind was chromatographed over silica gel (0.040–0.063 mm particle size) with tert.butyl methyl ether:n-hexane (2:3) as the eluent.
Yield: 528 mg (13%) of colorless resin
IR (film): 2738, 1781, 1744, 1717, 1690, 1496, 1178, 986 cm⁻¹
MS: (M+MH₄⁺) 425.6

EXAMPLE 11

(a) Benzhydryl (E)-(2S,3S,5R)-3-methyl-3-[2-(1,2,4-oxadiazol-3-yl)-vinyl]-7-oxo-4-thia-1-aza-bicyclo[3.2.0]heptane-2-carboxylate 1.14 g (3.0 mmol) of benzhydryl (2S,3R,5R)-3-formyl-3-methyl-7-oxo-4-thia-1-aza-bicyclo[3.2.0]heptane-2-carboxylate were dissolved in 15 ml of 1,2-butylene oxide, treated with 1.38 g (3.6 mmol) of (1,2,4-oxadiazol-3-yl)methyl-triphenylphosphonium chloride and refluxed for 10 hours. Subsequently, the mixture was filtered, the filtrate is evaporated and the residual brown oil was chromatographed over silica gel (0.040–0.063 mm particle size) with methylene chloride as the eluent.
Yield: 280 mg (21%) of colorless crystals
MS: (M+NH₄)⁺ 465.3
IR (KBr): 1792, 1753, 1658, 1492, 1200, 991 cm⁻¹

(b) Benzhydryl (E)-(2S,3S,5R)-3-methyl-3-[2-(1,2,4-oxadiazol-3-yl)-vinyl]-4,4,7-trioxo-4-thia-1-aza-bicyclo[3.2.0]heptane-2-carboxylate 280 mg (0.63 mmol) of benzhydryl (E)-(2S,3S,5R)-3-methyl-3-[2-(1,2,4-oxadiazol-3-yl)-vinyl]-7-oxo-4-thia-1-aza-bicyclo -[3.2.0]heptane-2-carboxylate were oxidized according to Example 8. Chromatography was carried out once over silica gel (particle size 0.040–0.063 mm) with ethyl acetate:n-hexane (9:16) as the eluent and crystallization was carried out from methylene chloride/n-hexane.
Yield: 95 mg (40%) of colorless crystals
MS: (M−H)⁻ 478.3
IR (KBr): 1805, 1758, 1650, 1334, 1196 cm⁻¹
M.p.: 157° C.
Elementary analysis: C₂₄H₂₁N₃O₆S(479.507)

Calc. C. 60.12 H 4.41 N 8.76
Found C. 59.94 H 4.26 N 8.55

(c) (E)-(2S,3S,5R)-3-methyl-3-[2-(1,2,4-oxadiazol-3-yl)-vinyl]-4,4,7-trioxo-4-thia-1-aza-bicyclo[3.2.0]heptane-2-carboxylic acid 355 mg (0.74 mmol) of benzhydryl (E)-(2S,3S,5R)-3-methyl-3-[2-(1,2,4-oxadiazol-3-yl)-vinyl]-4,4,7-trioxo-4-thia-1-aza-bicyclo[3.2.0]heptane-2-carboxylate were dissolved in 3 ml of m-cresol and stirred at 50° C. for 4 hours. 20 ml of n-hexane are added to the pale brown solution, the separated crystals were filtered off under suction and rinsed with n-hexane. The crude crystallizate was recrystallized from ethyl acetate/n-hexane.
Yield: 170 mg (73%) of colorless crystals
MS: (M−H)⁻ 312.2
IR (KBr): 2900(br), 1811, 1714, 1660, 1331, 1194, 980 cm⁻¹
M.p.: 161° C.(dec.)
Elementary analysis: C₁₁H₁₁N₃O₆S (313.284)

Calc. C. 42.17 H 3.54 N 13.41
Found C. 42.41H 3.64 N 13.18

(c) Sodium (EE)-(2S,3S,5R)-3-methyl-3-[2-(1,2,4-oxadiazol-3-yl)-vinyl]-4,4,7-trioxo-4-thia-1-aza-bicyclo[3.2.0]heptane-2-carboxylic acid 85 mg (0.27 mmol) of (E)-(2S,3S,5R)-3-methyl-3-[2-(1,2,4-oxadiazol-3-yl)-vinyl]-4,4,7-trioxo-4-thia-1-aza-bicyclo

[3.2.0]heptane-2-carboxylic acid were added in one portion to a clear solution of 23 mg (0.27 mmol) of sodium hydrogen carbonate in 10 ml of water, the mixture was stirred for about 10 minutes, filtered and lyophilized.
Yield: 90 mg (91%) of colorless lyophilizate
MS: (M–Na)⁻ 312.2
IR (KBr): 1787, 1627, 1395, 1321, 1192, 970 cm⁻¹
Elementary analysis: $C_{11}H_{10}N_3O_6SNa$ (335.266)
  Calc. C. 39.41 H 3.01 N 12.53
  Found#) C. 39.86 H 3.04 N 12.51
  #) anhydrous, calculated with 5.82% water

EXAMPLE 12

(a) Benzhydryl (E) and (Z)-(2S,3S,5R)-3-methyl-3-(2-thiazol- 2-yl-vinyl) -7-oxo-4-thia-1-aza-bicyclo [3.2. 0]heptane-2-carboxylate 1.14g (3.0 mmol) of benzhydryl (2S,3R,5R)-3-formyl-3-methyl-7oxo-4-thia-1-aza-bicyclo[3.2.0]heptane-2-carboxylate were dissolved in 50 ml of 1,2-butylene oxide, treated with 1.53 g (3.86 mmol) of (thiazol-2-yl)methyltriphenylphosphonium chloride and refluxed for 40 hours. Subsequently, the mixture was filtered, evaporated and the brown residue remaining behind was chromatographed over silica gel (0.040–0.063 mm particle size) with methylene chloride:ethyl acetate (95:5) as the eluent. The two isomers were separated in this manner, the Z isomer being eluted as the first component.

Z Isomer:
Yield: 240 mg (17%) of yellow oil
IR (film): 1778, 1743, 1493, 1197, 986 cm⁻¹
MS: (M+H⁺) 463.5

E Isomer:
Yield: 855 mg (62%) of yellow resin
IR (KBr): 1779, 1746, 1492, 1292, 988 cm⁻¹
MS: (M+H)+463.5

30(b) Benzhydryl (E)-(2S,3S,5R)-3-methyl-4,4,7-trioxo-3-(2-thiazol-2-yl-vinyl) -4-thia-1- aza-bicyclo [3.2.0]heptane-2-carboxylate 200 mg (0.43 mmol) of benzhydryl (E)-(2S,3S,5R)-3-methyl-3-(2-thiazol-2-yl-vinyl)-7-oxo-4-thia-1-aza-bicyclo [3.2.0]heptane-2carboxylate were oxidized according to Example 8. Chromatography was carried out over silica gel (particle size 0.040–0.063 mm) with methylene chloride-:ethyl acetate (95:5) as the eluent.
Yield: 72 mg (33%) colorless foam
MS: (M+H)+495.4
IR (KBr): 1799, 1756, 1329, 1192, 1142, 963 cm⁻¹

Benzhydryl (Z)-(2S,3S,5R)-3-methyl-4,4,7-trioxo-3-(2-thiazol-2-yl-vinyl)-4-thia-1-aza-bicyclo[3.2.0] heptane-2-carboxylate 210 mg (0.45 mmol) of benzhydryl (Z)-(2S,3S,5R)-3-methyl-4,4,7-trioxo-3-(2-thiazol-2-yl-vinyl)-4-thia-1-aza-bicyclo-[3.2.0]heptane-2-carboxylate are oxidized according to Example 8. Chromatography was carried out over silica gel (particle size 0.040–0.063 mm) with methylene chloride:ethyl acetate (95:5) as the eluent.
Yield: 72 mg (33%) of colorless foam
MS: (M+H)⁺ 495.4
IR (KBr): 1793, 1754, 1490, 1328, 1184, 1142, 963 cm⁻¹

(E)-(2S,3S,5R)-3-Methyl-4,4,7-trioxo-3-(2-thiazol-2-yl-vinyl)-4-thia-1-aza-bicyclo[3.2.0]heptane-2-carboxylic acid 200 mg (0.40 mmol) of benzhydryl (E)-(2S,3S,5R)-3-methyl-3-(2-thiazol-2-yl-vinyl)-4,4,7-trioxo-4-thia-1-aza-bicyclo-[3.2.0]heptane-2-carboxylate were deprotected analogously to Example 11.
Yield: 53 mg (40%) of colorless crystals
MS: (M+H)⁺ 329.4
IR (KBr): 2800(br), 1791, 1740, 1634, 1321, 1142, 965 cm⁻¹

Sodium (E)-(2S,3S,5R)-3-methyl-4,4,7-trioxo-3-(2-thiazol-2-yl-vinyl)-4-thia-1-aza-bicyclo [3.2.0] heptane-2-carboxylate 53 mg (0.16 mmol) of (E)-(2S,3S,5R)-3-methyl-4,4,7-trioxo-3-(2-thiazol-2-yl-vinyl) -4-thia-1-aza-bicyclo [3.2.0] heptane-2-carboxylic acid were converted into the corresponding sodium salt analogously to Example 11.
Yield: 55 mg (98%) of colorless lyophilizate
IR (KBr): 1778, 1627, 1392, 1318, 1192, 1141, 955 cm⁻¹
Elementary analysis: $C_{12}H_{11}N_2O_5S_2Na$ (350.339)
  Calc. C 41.14 H 3.16 N 8.00
  Found#) C 40.73 H 3.51 N 7.92
  #) anhydrous, calculated with 5.9% water Sodium (Z)-(2S,3S,5R)-3-methyl-4,4,7-trioxo-3-(2-thiazol-2-yl-vinyl)-4-thia-1-aza-bicyclo[3.2.0] heptane-2-carboxylate 160 mg (0.32 mmol) of benzhydryl (Z)-(2S,3S,5R)-3-methyl-4,4,7-trioxo-3-(2-thiazol-2-yl-vinyl)-4-thia-1-aza-bicyclo-[3.2.0]heptane-2-carboxylate were converted into the corresponding sodium salt analogously to Example 8.
Yield: 60 mg (57%) of colorless lyophilizate
IR (KBr): 1781, 1623, 1398, 1320, 1193, 1140, 950 cm⁻¹
¹H-NMR (250 MHz, CDCl₃): δ[ppm]=1.52(s,3H), 3.42(dd, 1H,J=16 Hz, 1.2 Hz,6-H), 3.58(dd,1H,J=16 Hz, 4.1Hz,6-H), 5.04(dd,1H,J=1.2 Hz, 4.1Hz,5-H), 5.19(s,1H,2-H), 6.06(d,1H,J=12.5 Hz,=CH), 7.14(d,1H,J=12.5 Hz,=CH), 7.75(AB system,2H,J=3.5 Hz, thiazole-H).

EXAMPLE 13

(a) Benzhydryl (E)-(2S,3S,5R)-3-methyl-3-(2-pyridin-2-yl-vinyl) -7-oxo-4-thia-1-aza-bicyclo [3.2.0]heptane-2-carboxylate A suspension of 353 mg (1.0 mmol) of (2-picolyl)methylene-triphenylphosphorane and 381 mg (1.00 mmol) of benzhydryl (2S,3R,5R)-3-formyl-3-methyl-7-oxo-4-thia-1-aza-bicyclo-[3.2.0]heptane-2-carboxylate in 10 ml of diethyl ether was stirred at room temperature under argon for 2 hours. The mixture was treated with 10 ml of methylene chloride, insoluble material was removed by suction filtration and the filtrate was concentrated. The residue remaining behind was chromatographed over silica gel (particle size 0.040–0.063 mm) with methylene chloride:ethyl acetate (95:5) as the eluent.
Yield: 128 mg (28%) of a colorless foam
MS: (M⁰) 456
IR (KBr): 1779, 1747, 1634, 1291, 988 cm⁻¹

(b) Benzhydryl (E)-(2S,3S,5R)-3-methyl-3-(2-pyridin-2-yl-vinyl)-4,4,7-trioxo-4-thia-1-aza-bicyclo [3.2.0]heptane-2-carboxylate 196 mg (0.43 mmol) of benzhydryl (E)-(2S,3S,5R)-3-methyl-3-(2-pyridin-2-yl-vinyl)-7-oxo-4-thia-1-aza-bicyclo [3.2.0]heptane-2carboxylate were oxidized according to Example 8. Chromatography was carried out over silica gel (particle size 0.040–0.063 mm) with methylene chloride-:ethyl acetate (95:5) as the eluent.
Yield: 130 mg (62%) of colorless foam MS: (M+H)⁺ 489.4
IR (KBr): 1799, 1756, 1580, 1490, 1327, 1184, 1141, 969 cm⁻¹

(c) (E)-(2S,3S,5R)-3-Methyl-3-(2-pyridin-2-yl-vinyl)-4,4,7-trioxo-4-thia-1-aza-bicyclo[3.2.0]heptane-2-carboxylic acid 200 mg (0.41 mmol) of benzhydryl (E)-(2S,3S,5R)-3-methyl-3-(2-pyridin-2-yl-vinyl)-4,4,7-trioxo-4-thia-1-aza-bicyclo[3.2.0]-heptane-2-carboxylate were deprotected analogously to Example 10.
Yield: 85 mg (65%) of pale beige crystal powder
MS: (M+H)⁺ 323.3
IR (KBr): 2700(br), 1790, 1720, 1621, 1318, 1140, 978 cm⁻¹

Sodium (E)-(2S,3S,5R)-3-methyl-3-(2-pyridin-2-yl-vinyl)-4,4,7trioxo-4-thia-1-aza-bicyclo[3.2.0]heptane-2-carboxylic acid 83 mg (0.17 mmol) of (E)-(2S,3S,5R)-3-methyl-3-(2-pyridin-2-yl-vinyl)-4,4,7-trioxo-4-thia-1-aza-bicyclo[3.2.0]heptane-2carboxylic acid were converted into the corresponding sodium salt analogously to Example 10.
Yield: 89 mg (100%) of colorless lyophilizate
IR (KBr): 1784, 1629, 1587, 1478, 1396, 1320, 1187, 1141, 980 cm⁻¹
Elementary analysis: $C_{14}H_{13}N_2O_5SNa$ (344.317)
Calc. C 48.84 H 3.81 N 8.14
Found#) C. 49.18 H 4.23 N 8.17
) anhydrous, calculated with 6.86% water

EXAMPLE 14

(a) Benzhydryl (E)-(2S,3S,5R)-3-[2-(methoxy-methyl-carbamoyl)-vinyl]-3-methyl-7-oxo-4-thia-1-aza-bicyclo[3.2.0]-heptane-2-carboxylate An orange solution of 1.14 g (3.0 mmol) of benzhydryl (2S,3R,5R)-3-formyl-3-methyl-7-oxo-4-thia-1-aza-bicyclo[3.2.0]heptane-2carboxylate and 1.14g (3.15 mmol) of (N-methoxymethylaminocarbonylmethylene)-triphenylphosphorane was stirred at room temperature under argon for 3 days. The solvent was removed on a rotary evaporator and the residue was chromatographed over silica gel (particle size 0.040–0.063 mm) with ethyl acetate:n-hexane (1:1) as the eluent.
Yield: 1.12 g (80%) of colorless foam
MS: (M+H)⁺ 467.4
IR (KBr): 1781, 1744, 1662, 1629, 995 cm⁻¹

(b) Benzhydryl (E)-(2S,3S,5R)-3-[2-(methoxy-methyl-carbamoyl)-vinyl]-3-methyl-4,4,7-trioxo-4-thia-1-aza-bicyclo[3.2.0]heptane-2-carboxylate 0.69 g (1.48 mmol) of benzhydryl (E)-(2S,3S,5R)-3-[2-(methoxy-methyl-carbamoyl)-vinyl]-3-methyl-7-oxo-4-thia-1-aza-bicyclo[3.2.0]heptane-2-carboxylate was oxidized in analogy to Example 8. Chromatography was carried out over silica gel (particle size 0.040–0.063 mm) with ethyl acetate:n-hexane (3:2) as the eluent.
Yield: 405 mg (55%) of colorless foam
MS: (M+H)⁺ 499.4
IR (KBr): 1807, 1753, 1662, 1624, 1318, 1140, 1000 cm⁻¹

(c) Sodium (E)-(2S,3S,5R)-3-[2-(methoxy-methyl-carbamoyl)-vinyl]- 3-methyl-4,4,7-trioxo-4-thia-1-aza-bicyclo [3.2.0]-heptane-2-carboxylate.

200 mg (0.40 mmol) of benzhydryl (E)-(2S,3S,5R)-3-[2-(methoxy-methyl-carbamoyl)vinyl]-3-methyl-4,4,7-trioxo-4-thia-1-aza-bicyclo[3.2.0]heptane-2-carboxylate were deprotected according to Example 8.
Yield: 95 mg (67%) of colorless lyophilizate
MS: (M+H)⁺ 355.3
IR (KBr): 1785, 1650, 1626, 1390, 1322, 1191, 1141, 980 cm⁻¹
Elementary analysis: $C_{12}H_{15}N_2O_7SNa$ (354.309)
Calc. C 40.68 H 4.27 N 7.91
Found#) C. 40.37 H 4.35 N 7.84
) anhydrous, calculated with 2.74% water

EXAMPLE 15

(E)-(2S,3S,5R)-3-Methyl-3-[2-(1-methyl-pyridin-2-ylio)-vinyl]-4,4,7-trioxo-4-thia-1-aza-bicyclo[3.2.0]heptan-2-carboxylic acid 150 mg (0.31 mmol) of benzhydryl (E)-(2S,3S,5R)-3-methyl-3-(2-pyridin-2-yl-vinyl)-4,4,7-trioxo-4-thia-1-aza-bicyclo[3.2.0]heptane-2-carboxylic acid were dissolved in 3 ml of methylene chloride, cooled to 0° C. and treated with 56 µl (0.51 mmol) of methyl trifluoromethylsulfonate. The cooling bath was removed and the mixture was stirred at room temperature for 2 days. The solvent was removed on a rotary evaporator and the residue was dried in a high vacuum. The thus-obtained product (200 mg, 100%) was processed without further purification. The brown resin was dissolved in 2 ml of m-cresol and stirred at 50° C. for 2 hours. Thereafter, the mixture was treated with 10 ml of isobutyl methyl ketone as well as 5 ml of water, shaken, the phases were separated and the organic phase was extracted twice with 5 ml of water. The aqueous phases were washed twice with 10 ml of isobutyl methyl ketone each time, filtered and lyophilized. The yellowish lyophilizate was chromatographed over polymeric hydrophobic gel with water as the eluent.
Yield: 105 mg (72%) of orange lyophilizate
IR (KBr): 1778, 1627, 1377, 1185, 970 cm⁻¹
MS: (M+) 337.4

EXAMPLE 16

(a) Benzhydryl (1E,3E)-(2S,3S,5R)-3-(4-formyl-buta-1,3-dienyl)-3-methyl-7-oxo-4-thia-1-aza-bicyclo[3.2.0]heptane-2-carboxylate Benzhydryl (1E,3E)-(2S,3S,5R)-3-(4-formyl-buta-1,3-dienyl)-3-methyl-7-oxo-4-thia-1-aza-bicyclo[3.2.0]heptane-2-carboxylate was prepared in analogy to Example 9 from 3.81 g (10.0 mmol) of benzhydryl (2S,3R,5R)-3-formyl-3-methyl-7-oxo-4-thia-1-azabicyclo[3.2.0]heptane-2-carboxylate and 4.55 g (15.0 mmol) of formylmethylene-triphenylphosphorane. Chromatography was carried out over silica gel (0.040–0.063 mm particle size) with methylene chloride:ethyl acetate (98:2) as the eluent.
Yield: 347 mg (8%) of yellowish resin
MS: (M+NH₄)⁺ 451.4
IR (KBr): 1779, 1745, 1680, 1637, 1201, 988 cm⁻¹

EXAMPLE 17

(a) Benzhydryl (1E,3E) and (1E,3Z)-(2S,3S,5R)-3-(4-cyano-buta-1,3-dienyl)-3-methyl-7-oxo-4-thia-1-aza-bicyclo-[3.2.0]heptane-2-carboxylate Benzhydryl (1E,3E) and (1E,3Z)-(2S,3S,5R)-3-(4-cyano-buta-1,3-dienyl)-3-methyl-7-oxo-4-thia-1-aza-bicyclo [3.2.0]heptane-2-carboxylate was prepared in analogy to Example 4, Method B, from 815 mg (2.14 mmol) of benzhydryl (1E,3E)-(2S,3S,5R)-3-(4-formyl-buta-1,3-dienyl)-3-methyl-7-oxo-4-thia-1-aza-bicyclo-[3.2.0] heptane-2-carboxylate. The residual oil was purified over silica gel (particle size 0.040–0.063 mm) with ethyl acetate:n-hexane (1:2) as the eluent.
Yield: 820 mg (89%) of isomer mixture, E:Z 2:3
Spectroscopic data of the isomer mixture:
IR (film): 2215, 1780, 1745, 1202, 989 cm$^{-1}$
MS: (M+NH$_4^+$) 448.5

(b) Benzhydryl (1E,3E) and (1E,3Z)-(2S,3S,5R)-3-(4-cyano-buta-1,3-dienyl)-3-methyl-4,4,7-trioxo-4-thia-1-aza-bicyclo[3.2.0]heptane-2-carboxylate 770 mg (1.79 mmol) of benzhydryl (1E,3E) and (1E,3Z)-(2S,3S,5R)-3-(4-cyano-buta-1,3-dienyl)-3-methyl-7-oxo-4-thia-1-aza-bicyclo[3.2.0]heptane-2-carboxylate were oxidized according to Example 8. The two isomers can be separated by chromatography over silica gel (particle size 0.040–0.063 mm) with ethyl acetate:n-hexane (9:16) as the eluent. The Z isomer was eluted as the first component.
Yield:
Z: 430 mg (52%) of colorless oil
E: 280 mg (34%) of colorless foam
Spectroscopic data E isomer:
MS: (M+NH$_4$)$^+$ 480.5
IR (KBr): 2219, 1800, 1756, 1329, 1191, 994 cm$^{-1}$
Spectroscopic data Z isomer:
MS: (M+NH$_4$)$^+$ 435.3
IR (KBr): 2210, 1800, 1756, 1330, 1192, 993 cm$^{-1}$ (c) Sodium (1E,3E)-(2S,3S,5R)-3-(4-cyano-buta-1,3-dienyl)-3-methyl-4,4,7-trioxo-4-thia-1-aza-bicyclo[3.2.0]heptane-2-carboxylate 250 mg (0.54 mmol) of benzhydryl(1E,3E)-(2S,3S,5R)-3-(4-cyano-buta-1,3-dienyl)-3-methyl-4,4,7-trioxo-4-thia-1-aza-bicyclo[3.2.0]heptane-2-carboxylate were deprotected in analogy to Example 8.
Yield: 55 mg (41%) of yellowish lyophilizate
IR (KBr): 2221, 1781, 1631, 1397, 1319, 1139, 992 cm$^{-1}$
MS: (M+Na)+341.2

Sodium (1E,3Z)-(2S,3S,5R)-3-(4-cyano-buta-1,3-dienyl)-3-methyl-4,4,7-trioxo-4-thia-1-aza-bicyclo[3.2.0]heptane-2-carboxylate 230 mg (0.49 mmol) of benzhydryl (1E,3E)-(2S,3S,5R)-3-(4-cyano-buta-1,3-dienyl)-3-methyl-4,4,7-trioxo-4-thia-1-aza-bicyclo[3.2.0]heptane-2-carboxylate were deprotected in analogy to Example 8.
Yield: 84 mg (58%) of yellowish lyophilizate
IR (KBr): 2219, 1780, 1625, 1396, 1316, 1138, 951 cm$^{-1}$
MS: (M+H)$^+$ 319.3
Elementary analysis: C$_{12}$H$_{11}$N$_2$O$_5$SNa (318.279)
Calc. C 45.28 H 3.48 N 8.80
Found#) C. 45.29 H 3.63 N 8.82
) anhydrous, calculated with 6.93% water

EXAMPLE 18

(a) Benzhydryl (E/Z)-(2S,3S,5R)-3-methyl-7-oxo-3-[2-oxo-1-(2,2,2-trifluoroethyl)-pyrrolidin-3-ylidenmethyl]-4-thia-1-aza-bicyclo[3.2.0]heptane-2-carboxylate 762 mg (2.0 mmol) of benzhydryl (2S,3R,5R)-3-formyl-3-methyl-7-oxo-4-thia-1-aza-bicyclo[3.2.0]heptane-2-carboxylate were reacted with 1.02 g (2.0 mmol) of rac-[2-oxo-1(2,2,2-trifluoroethyl)-2-pyrrolidinyl]-triphenylphosphonium bromide according to Example 12. Chromatography was carried out over silica gel (particle size 0.040–0.063 mm) with ethyl acetate:n-hexane (9:16) as the eluent.
Yield: 763 mg (71%) of isomer mixture, E:Z 5:1
Spectroscopic data of the mixture:
IR (film): 1782, 1748, 1702, 1664, 1158 cm$^{-1}$
MS: (M-CPh$_2$) 363

(b) Benzhydryl (E) und (Z)-(2S,3S,5R)-3-methyl-3-[2-oxo-1-(2,2,2-trifluoroethyl)-pyrrolidin-3-ylidenemethyl]-4,4,7-trioxo-4-thia-1-aza-bicyclo[3.2.0]heptane-2-carboxylate 763 mg (1.42 mmol) of benzhydryl (E/Z)-(2S,3S,5R)-3-methyl-7-oxo-3-[2-oxo-1-(2,2,2-trifluoroethyl)-pyrrolidin-3-ylidenemethyl]-4-thia-1-aza-bicyclo[3.2.0]heptane-2-carboxylate were oxidized according to Example 8. The two isomers were separated by chromatography over silica get (particle size 0.040–0.063 mm) with ethyl acetate:n-hexane (1:2) as the eluent.
Yield:
E: 192 mg (24%) of colorless foam
Z: 32 mg (4%) of colorless foam
Spectroscopic data E isomer:
MS: (M+NH$_4$)$^+$ 580.4
IR (KBr): 1801, 1759, 1706, 1667, 1329, 1144 cm$^{-1}$
Spectroscopic data Z isomer:
MS: (M+NH$_4$)$^+$ 580.4
IR (KBr): 1798, 1755, 1694, 1327, 1142 cm$^{-1}$ (c) (E)-(2S,3S,5R)-3-Methyl-3-[2-oxo-1-(2,2,2-trifluoro-ethyl)-pyrrolidin-3-ylidenemethyl]-4,4,7-trioxo-4-thia-1-aza-bicyclo[3.2.0]heptane-2-carboxylic acid 192 mg (0.34 mmol) of benzhydryl (E)-(2S,3S,SR)-3-methyl-3-[2-oxo-1-(2,2,2-trifluoro-ethyl)-pyrrolidin-3-ylidenemethyl]-4,4,7-trioxo-4-thia-1-aza-bicyclo[3.2.0]heptane-2-carboxylate were deprotected analogously to Example 11.
Yield: 78 mg (59%) of colorless crystal powder
MS: (M+NH$_4$)$^+$ 414.4
IR (KBr): 2800(br), 1790, 1729, 1674, 1646, 1321, 1166 cm$^{-1}$ Sodium (E)-(2S,3S,5R)-3-methyl-3-[2-oxo-1-(2,2,2-trifluoro-ethyl)-pyrrolidin-3-ylidenemethyl]-4,4,7-trioxo-4-thia-1-aza-bicyclo[3.2.0]heptane-2-carboxylate 0mg (0.13 mmol) of (E)-(2S,3S,5R)-3-methyl-3-[2-oxo-1-(2,2,2trifluoro-ethyl)-pyrrolidin-3-ylidenemethyl-4,4,7-trioxo -4-thia-1-aza-bicyclo[3.2.0]heptane-2-carboxylic acid were converted into the corresponding sodium salt analogously to Example 11.
Yield: 52 mg (98%) of colorless lyophilizate
IR (KBr): 1780, 1699, 1628, 1478, 1396, 1323, 1140 cm$^{-1}$
Elementary analysis: C$_{14}$H$_{14}$N$_2$O$_6$F$_3$SNa (418.318)
Calc. C 40.20 H 3.37 N 6.70
Found#) C. 39.80 H 3.28 N 6.62
) anhydrous, calculated with 7.24% water

EXAMPLE 19

(a) Benzhydryl (E/Z)-(2S,3S,5R)-3-(1-cyclopropyl-2-oxo-pyrrolidin-3-ylidenemethyl)-3-methyl-7-oxo-4-thia-1-aza-bicyclo [3.2.0]heptane-2-carboxylate 381 mg (1.0 mmol) of benzhydryl (2S,3R,5R)-3-formyl-3-methyl-7-oxo-4-thia-1-aza-bicyclo[3.2.0]heptane-2- carboxylate were reacted with 495 mg (1.1 mmol) of rac-[1-cyclopropyl-2-oxo-3pyrrolidinyl]-triphenylphosphonium bromide according to Example 18. Chromatography was carried out over silica gel (particle size 0.040–0.063 mm) with ethyl acetate:n-hexane (9:16) as the eluent.
Yield: 362 mg (74%) of isomer mixture, E:Z 5:1
Spectroscopic data of the mixture:
IR (film): 1780, 1750, 1692, 1661, 1195, 1118 cm$^{-1}$
MS: (M+H)$^+$ 489.4

EXAMPLE 20

(a) Benzhydryl (E)-(2S,3S,5R)-3-(3-hydroxy-propen-1-yl)-3-methyl-7-oxo-4-thia-1-aza-bicyclo [3.2. 0]heptane-2-carboxylate 5.80 g (14.2 mmol) of benzhydryl (E)-(2S,3S,5R)-3-(2-formyl-vinyl)-3-methyl-7-oxo-4-thia-1-aza-bicyclo[3.2.0]heptane-2carboxylate were dissolved in 240 ml of toluene under argon and is cooled to 0° C. Then, 14.2 ml (21.3 mmol) of a 20% diisobutylaluminium hydride solution (in toluene) were added dropwise and the cooling bath is removed. The reaction mixture was stirred at room temperature for 6 hours, poured into 150 ml of saturated ammonium chloride solution and extracted three times with 200 ml of methylene chloride each time. The combined organic extracts were washed once with 300 ml of water as well as saturated sodium chloride solution, dried over magnesium sulfate, filtered and freed from solvent on a rotary evaporator. The residual yellow oil was chromatographed over silica gel (particle size 0.040–0.063 mm) with ethyl acetate:n-hexane (9:16) as the eluent.
Yield: 1.90 g (32%) of colorless resin
IR (film): 3480(br), 1778, 1750, 1202, 1080, 988 cm$^{-1}$
MS: (M+NH$_4$)$^+$ 427.6

(c) Sodium (E)-(2S,3S,5R)-3-(3-hydroxy-propen-1-yl)-3-methyl-4,4,7-trioxo-4-thia-1-aza-bicyclo [3.2.0]heptane-2-carboxylate 500 mg (0.95 mmol) of benzhydryl (E)-(2S,3S,5R)-3-methyl-4,4,7-trioxo-3-[3-[(R)- and (S)-tetrahydro-pyran-2-yloxy]-propenyl]-4-thia-1-aza-bicyclo[3.2.0]heptane-2-carboxylate were deprotected according to Example 8.
Yield: 165 mg (62%) of colorless lyophilizate
MS: (M-Na)$^-$ 274.3
IR (KBr): 3428, 1780, 1622, 1398, 1311, 1192, 1139, 1082 cm$^{-1}$
Elementary analysis: C$_{10}$H$_{12}$NO$_6$SNa (297.257)
Calc. C 40.41H 4.07 N 4.71
Found#) C. 40.44 H 4.48 N 4.79
) anhydrous, calculated with 8.73% water
Benzhydryl (E)-(2S,3S,5R)-3-methyl-7-oxo-3-[3-[(R)- and (S)-tetrahydro-pyran-2-yloxy]-propenyl]-4-thia-1-aza-bicyclo-[3.2.0]heptane-2-carboxylate 620 mg (1.50 mmol) of benzhydryl (E)-(2S,3S,5R)-3-(3-hydroxy-propenyl)-3-methyl-7-oxo-4-thia-1-aza-bicyclo [3.2.0]heptane-2carboxylate were dissolved in 30 ml of methylene chloride and treated with 4.5 mg (0.024 mmol) of p-toluenesulfonic acid monohydrate. Subsequently, 0.25 ml (2.70 mmol) of 3,4-dihydro-2H-pyran was added and the mixture was stirred for a further 1 hour. The solvent was removed on a rotary evaporator and chromatography was carried out over silica gel (particle size 0.040–0.063 mm) with ethyl acetate:n-hexane (9:16) as the eluent.
Yield: 700 mg (93%) colorless oil, diastereomer mixture (1:1)
IR (film): 3031, 1782, 1749, 1257, 1134, 967 cm$^{-1}$
MS: (M+NH$_4$)$^+$ 511.6

Benzhydryl (E)-(2S,3S,5R)-3-methyl-4,4,7-trioxo-3-[3-[(R)- und (S)-tetrahydropyran-2-yloxy]propenyl]-4-thia-1-aza-bicyclo-[3.2.0]heptane-2-carboxylate 585 mg (1.18 mmol) of benzhydryl (E)-(2S,3S,5R)-3-methyl-7-oxo-3-[3-[(R)- and (S)-tetrahydropyran-2-yloxy]propenyl]-4-thia-1-aza-bicyclo-[3.2.0]heptane-2-carboxylate were oxidized according to Example 8. Chromatography was carried out over silica gel (particle size 0.040–0.063 mm) with ethyl acetate:n-hexane (9:16) as the eluent.
Yield: 525 mg (84%) of colorless foam, diastereomer mixture (1:1)
IR (KBr): 1800, 1756, 1327, 1189, 1141, 969 cm$^{-1}$
MS: (M+NH$_4$)$^+$ 543.5

EXAMPLE 21

(a) Benzhydryl (E)-(2S,3S,5R)-3-[3-(2-chloro-acetylamino-carbonyloxy)-propenyl]-3-methyl-7-oxo-4-thia-1-aza-bicyclo-[3.2.0]heptane-2-carboxylate 300 mg (0.73 mmol) of benzhydryl (E)-(2S,3S,5R)-3-(3-hydroxy-propenyl)-3-methyl-7-oxo-4-thia-1-aza-bicyclo [3.2.0]heptane-2carboxylate were dissolved in 10 ml of tetrahydrofuran under argon and treated with 90 µl (1.05 mmol) of chloroacetyl isocyanate. The mixture was stirred for 3 hours, evaporated and chromatography was carried out over silica gel (particle size 0.040–0.063 mm) with ethyl acetate:n-hexane (9:16) as the eluent.
Yield: 300 mg (77%) of colorless foam
IR (KBr): 3300(br), 1779, 1753, 1730, 1495, 1203 cm$^{-1}$
MS: (M+NH$_4$)$^+$ 546.4

(b) Benzhydryl (E)-(2S,3S,5R)-3-[3-(2-chloro-acetylamino-carbonyloxy)-propenyl]-3-methyl-4,4,7-trioxo-4-thia-1-aza-bicyclo [3.2.0]heptane-2-carboxylate 295 mg (0.57 mmol) of benzhydryl (E)-(2S,3S,5R)-3-[3-(2-chloro-acetylaminocarbonyloxy)-propenyl]-3-methyl-7-oxo-4-thia-1-aza-bicyclo[3.2.0]heptane-2-carboxylate were oxidized analogously to Example 8. Chromatography was carried out over silica gel (particle size 0.040–0.063 mm) with ethyl acetate:n-hexane (9:16) as the eluent.
Yield: 216 mg (68%) of colorless foam
IR (KBr): 3413(br), 1798, 1758, 1730, 1705, 1326, 1198, 991 cm$^{-1}$
MS: (M+NH$_4$)$^+$ 578.4

(c) Sodium (E)-(2S,3S,5R)-3-[3-(2-chloro-acetylamino-carbonyloxy)-propenyl]-3-methyl-4,4,7-trioxo-4-thia-1-aza-bicyclo [3.2.0]heptane-2-carboxylate 195 mg (0.35 mmol) of benzhydryl (E)-(2S,3S,5R)-3-[3-(2-chloro-acetylaminocarbonyloxy)-propenyl]-3-methyl-4,4,7-trioxo-4-thia-1-aza-bicyclo[3.2.0]heptane-2-carboxylate were deprotected in analogy to Example 8 and converted into the corresponding sodium salt.
Yield: 60 mg (49%) of colorless lyophilizate
MS: (M—COCH$_2$Cl—Na)$^-$ 317.3
IR (KBr): 3435, 1781, 1721, 1622, 1533, 1396, 1314, 1192, 1139 cm$^{-1}$
$^1$H-NMR (250 MHz, D$_2$O): δ[ppm]=1.61(s,3H), 3.42(dd, 1H,J=16 Hz, 1.6 Hz, 6-H), 3.69(dd, 1H, J=16 Hz, 4.0 Hz, 6-H), 4.43(s,2H,CH$_2$Cl), 4.49(s,1H,2-H), 4.84(d,2H,J= 4.4 Hz,CH$_2$O), 5.08(dd,J=1.6 Hz, 4.0 Hz, 5-H), 6.08(d (br), 1H,J=16 Hz,=CH), 6.22(dt,1H,J=16 Hz, 4.4 Hz, =CH)

EXAMPLE 22

Benzhydryl (E)-(2S,3S,5R)-3-(carbamoyloxy-propenyl)-3-methyl-4,4,7-trioxo-4-thia-1-aza-bicyclo [3.2.0]heptane-2-carboxylate 450 mg (0.80 mmol) of benzhydryl (E)-(2S,3S,5R)-3-[3-(2-chloro-acetylaminocarbonyloxy)-propenyl]-3-methyl-4,4,7-trioxo-4-thia-1-aza-bicyclo[3.2.0]heptane-2-carboxylate were dissolved in 5 ml of tetrahydrofuran under argon and treated with 1.7 ml of methanol. 135 mg (1.61 mmol) of sodium hydrogen carbonate in 2.8 ml of water were added to this solution. After completion of the reaction (tlc control) the solvent mixture was removed on a rotary evaporator, the residual yellow oil was taken up in 15 ml of ethyl acetate as well as 15 ml of saturated sodium chloride solution, shaken and the phases were separated. The aqueous phase was back-extracted twice with 15 ml of ethyl acetate each time and the combined organic extracts were washed once with 15 ml of saturated sodium chloride solution. They were dried over magnesium sulfate, concentrated on a rotary evaporator and the residual oil was chromatographed over silica gel (particle size 0.040–0.063 mm) with ethyl acetate:n-hexane (2:1) as the eluent.

Yield: 200 mg (78%) of colorless foam
IR (KBr): 3481, 1799, 1749, 1731, 1601, 1329, 1191, 996 cm$^{-1}$
MS: (M+NH$_4$)$^+$ 484

(c) Sodium (E)-(2S,3S,5R)-3-(carbamoyloxy-propenyl)-3-methyl-4,4,7-trioxo-4-thia-1-aza-bicyclo [3.2.0]heptane-2-carboxylate 190 mg (0.60 mmol) of benzhydryl (E)-(2S,3S,5R)-3-(carbamoyl-oxypropenyl)-3-methyl-4,4,7-trioxo-4-thia-1-aza-bicyclo[3.2.0]heptane-2-carboxylate were deprotected in analogy to Example 8.

Yield: 82 mg (62%) of colorless lyophilizate
$^1$H-NMR (250 MHz, D$_2$O): δ[ppm]=1.61(s,3H), 3.42(dd, 1H,J=17 Hz, 1.6 Hz,6-H), 3.69(dd,1H,J=17 Hz,4 Hz,6-H), 4.48(s,1H,2-H), 4.70 (d,2H,J=4.6 Hz,CH$_2$), 5.08(dd, 1H,J=4 Hz, 1.6 Hz,5-H), 5.97 (d,1H,J=16 Hz,=CH), 6.19(dt,1H,J=16 Hz, 4.6 Hz,=CH).

EXAMPLE 23

(a) (2S ,3S ,5R)-1-[3-(2-Benzhydryloxycarbonyl-3-methyl-7-oxo-4-thia-1-aza-bicyclo[3.2.0]heptan-3-yl)-allyl]-pyridinium trifluormethanesulfonate 410 mg (1.0 mmol) of benzhydryl (E)-(2S,3S,5R)-3-(3-hydroxy-propenyl)-3-methyl-7-oxo-4-thia-1-aza-bicyclo [3.2.0]heptane-2carboxylate were dissolved in 6 ml of methylene chloride, cooled to –40° C. and treated with 250 μl (1.5 mmol) of trifluoromethanesulfonic anhydride. After 5 minutes 200 μl (2.50 mmol) of pyridine were added, the mixture was stirred at the same temperature for a further hour and subsequently the cooling bath was removed. The solvent was removed on a rotary evaporator at room temperature, the reaction mixture was taken up in 20 ml of methylene chloride and washed twice with 10 ml of saturated sodium chloride solution each time. Drying over magnesium sulfate, filtration and concentration on a rotary evaporator were carried out. The residual red resin was oxidized without further purification.

Yield: 600 mg (97%) of red resin
MS: (M$^+$) 471.6
IR (KBr): 1777, 1743, 1630, 1160, 987 cm$^{-1}$ (b) (2S,3S,5R)-1-[3-(2-Benzhydryloxycarbonyl-3-methyl-4,4,7-trioxo-4-thia-1-aza-bicyclo[3.2.0]-heptan-3-yl)-allyl]-pyridinium trifluoromethanesulfonate 600 mg (0.97 mmol) of (2S,3S,5R)-1-[3-(2-benzhydryloxycarbonyl-3-methyl-7-oxo-4-thia-1-aza-bicyclo[3.2.0]heptan-3-yl)-allyl]pyridinium trifluoromethanesulfonate were oxidized in analogy to Example 8.
Yield: 440 mg (70%) of green resin
MS: (M$^+$) 503.3
IR (KBr): 1797, 1753, 1632, 1167 cm$^{-1}$ (E)-(2S ,3S,5R)-3-Methyl-4,4,7-trioxo-3-(3-pyridin-1-ylio-propenyl)-4-thia-1-aza-bicyclo[3.2.0]heptane-2-carboxylate A solution of 440 mg (0.67 mmol) of (2S,3S,5R)-1-[3-(2-benzhydryloxycarbonyl-3-methyl-4,4,7-trioxo-4-thia-1-aza-bicyclo[3.2.0]heptan-3-yl)-allyl]-pyridinium trifluoromethane-sulfonate in 3 ml of m-cresol was stirred at 50° C. for 1.5 hours. The mixture was diluted with 10 ml of isobutyl methyl ketone at room temperature and extracted three times with 8 ml of water each time. The combined aqueous extracts were washed twice with 10 ml of isobutyl methyl ketone each time, filtered over a paper filter and lyophilized. The brown lyophilizate was subsequently chromatographed over polymeric hydrophobic gel with water as the eluent.

Yield: 125 mg (55%) of beige lyophilizate
IR (KBr): 1780, 1625, 1485, 1372, 1312, 980 cm$^{-1}$
MS: M+H$^+$337.4

We claim:
1. A compound of the formula

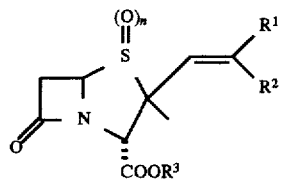

wherein
one of R$^1$ and R$^2$ is —COR$^4$, —CN, —CH$_2$R$^5$, halogen, —CH=CHR$^6$ or Q and the other is hydrogen or lower alkyl or both R$^1$ and R$^2$ together form a γ-lactam ring, R$^3$ is hydrogen, lower alkyl, aryl-alkyl, allyl or a residue which is cleavable in vivo, R$^4$ is lower alkyl, benzyloxy, amino, lower alkylamino or lower alkyl-lower alkoxyamino, R$^5$ is —OCONHR$^7$, —OCONH$_2$ or a five- or six-membered hetero-aromatic ring which contains at least one heteroatom selected from N, S and O and which is linked via a nitrogen atom, R$^6$ is —CN or —CHO, R$^7$ is —COCH$_2$Cl, Q is a five- or six-membered hetero-aromatic ring which contains at least one heteroatom selected from N, S and O and n is 2, and the pharmaceutically compatible salts thereof.

2. The compound according to claim 1, wherein
one of R$^1$ and R$_2$ is —COR$^4$, —CN or —CH$_2$OR$^5$ and the other is hydrogen or lower alkyl, R$^3$ is hydrogen, lower alkyl, aryl-alkyl, allyl or a residue which is cleavable in vivo, R$^4$ is lower alkyl, benzyloxy, amino or lower alkylamino, R$^5$ is —OCONH$_2$, R$^6$ is lower alkyl and n is 2.

3. The compound according to claim 1, wherein R$^1$ is CN, halogen or COR$^4$.

4. The compound according to claim 3 wherein $R^2$ is hydrogen.

5. The compound according to claim 4 wherein $R^4$ is methyl, benzyloxy, or amino.

6. The compound according to claim 5 wherein $R^3$ is hydrogen or benzhydryl.

7. The compound according to claim 6, Benzhydryl (E)-(2S,3S,5R)-3-(2-cyanoethenyl)-3-methyl-4,4,7-trioxo-4-thia-1-aza-bicyclo[3.2.0]heptane-2-carboxylate.

8. The compound according to claim 6, Benzhydryl (Z)-(2S,3S,5R)-3-(2-cyanoethenyl)-3-methyl-4,4,7-trioxo-4-thia-1-aza-bicyclo[3.2.0]heptane-2-carboxylate.

9. The compound according to claim 6, Sodium (E)-(2S, 3S,5R)-3-(2-cyanoethenyl)-3-methyl-4,4,7-trioxo-4-thia-1-aza-bicyclo[3.2.0]heptane-2-carboxylate.

10. The compound according to claim 6, Sodium (Z)-(2S, 3S,5R)-3-(2-cyanoethenyl)-3-methyl-4,4,7-trioxo-4-thia-1-aza-bicyclo[3.2.0]heptane-2-carboxylate.

11. The compound according to claim 6, Sodium (E)-(2S, 3S,5R)-3-(2-chloro-vinyl)-3-methyl-4,4,7-trioxo-4-thia-1-aza-bicyclo [3.2.0]heptane-2-carboxylate.

12. The compound according to claim 6, Sodium (E)-(2S, 3S,5R)-3-methyl-3-(3-oxo-but-1-enyl)-4,4,7-trioxo-4-thia-1-aza-bicyclo[3.2.0]-heptane-2-carboxylate.

13. The compound according to claim 6 selected from Benzhydryl (E)-(2S,3S,5R)-3-(2-carbamoyl-vinyl)-3-methyl-4,4,7-trioxo-4-thia-1-aza-bicyclo-[3.2.0]heptane-2-carboxylate, benzhydryl (Z)-(2S,3S,5R)-3-(2-carbamoyl-vinyl)-3-methyl-4,4,7-trioxo-4-thia-1-aza-bicyclo[3.2.0] heptane-2-carboxylate, and benzhydryl (E)-(2S,3S,5R)-3-(2-benzyloxycarbonyl-vinyl)-3-methyl-4,4,7-trioxo-4-thia-1-aza-bicyclo [3.2.0]heptane-2-carboxylate.

14. The compound according to claim 6 selected from Sodium (E)-(2S,3 S,5R)-3-(2-carbamoyl-vinyl)-3-methyl-4, 4,7-trioxo-4-thia-1-aza-bicyclo [3.2.0]heptane-2-carboxylate, sodium (Z)-(2S,3S,5R)-3-(2-carbamoyl-vinyl)-3-methyl-4,4,7-trioxo-4-thia-1-aza-bicyclo[3.2.0]heptane-2-carboxylate, and sodium (E)-(2S,3S,5R)-3-(2-benzyloxycarbonyl-vinyl)-3-methyl-4,4,7-trioxo-4-thia-1-aza-bicyclo[3.2.0] heptane-2-carboxylate.

15. A pharmaceutical composition which comprises a therapeutically effective amount of a compound having the formula

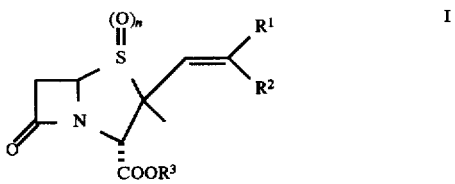

wherein
one of $R^1$ and $R^2$ is —$COR^4$, —CN, —$CH_2R^5$, halogen, —CH=$CHR^6$ or Q and the other is hydrogen or lower alkyl or both R1 and R2 together form a γ-lactam ring, $R^3$ is hydrogen, lower alkyl, aryl-alkyl, allyl or a residue which is cleavable in vivo, $R^4$ is lower alkyl, benzyloxy, amino, lower alkylamino or lower alkyl-lower alkoxyamino, $R^5$ is —$OCONHR^7$, —$OCONH_2$ or a five- or six-membered hetero-aromatic ring which contains at least one heteroatom selected from N, S and O and which is linked via a nitrogen atom, $R^6$ is —CN or —CHO, $R^7$ is —$COCH_2Cl$, Q is a five- or six-membered hetero-aromatic ring which contains at least one heteroatom selected from N, S and O and n is 2, and the pharmaceutically compatible salts thereof, and a pharmaceutically acceptable carrier.

16. The pharmaceutical composition of claim 15, further comprising an antibacterial effective amount of a β-lactam antibiotic, and their pharmaceutically compatible salts.

17. The pharmaceutical composition of claim 16, wherein the β-lactam antibiotic is selected from penicillins, cephalosporins, and penems and carbapenems.

18. The pharmaceutical composition of claim 17, wherein the β-lactam antibiotic is a penicillin.

19. The pharmaceutical composition of claim 18, wherein the penicillin is selected from the group piperacillin, mezlocillin, azlocillin, apalcillin, benzylpenicillin, phenoxymethylpenicillin, carbenicillin, methicillin, propicillin, tricarcillin, ampicillin, amoxicillin, mecillinam, aspoxicillin, azidocillin, bacampicillin, carfecillin sodium, carindacillin, clometocillin, cloxacillin, cyclacillin, dicloxacillin, diphenicillin sodium, epicillin, fenbencillin, floxacillin, hetacillin, lenampicillin, metampicillin, nafcillin sodium, oxacillin, penamecillin, penethamate hydriodid, penicillin G benethamine, penicillin G benzathine, penicillin benzhydrylamine, penicillin G calcium, penicillin G hydrabamine, penicillin G potassium, penicillin G procaine, penicillin N, penicillin O, penimepicycline, phenethicillin potassium, pivampicillin, quinacillin, sulbenicillin, talampicillin, temocillin, and ticarcillin.

20. The pharmaceutical composition of claim 17, wherein the β-lactam antibiotic is a cephalosporin.

21. The pharmaceutical composition of claim 20, wherein the cephalosporin is selected from the group ceftriazone, ceftazidime, cefetamet, cefatamet pivoxil, cefotaxime, cefmenoxime, ceftizoxime, cefuroxime, cephaloridine, cephalotin, cefazolin, cephalexin, cefoxitin, cephacetrile, cefamandole, cephapirin, cephradine, cephaloglycine, cefpirome, cefepime, cefaclor, cefadroxil, cefatrizine, cefazedone, cefixime, cefodizime, cefonicid, cefoperazone, ceforanide, cefotiam, cefpimizole, cefpiramide, cefpodoxime proxetil, cefroxadine, cefsulodin, cefteram, ceftezole, ceftibuten, cefuzonam, cephalosporin C, and pivcefalexin.

22. The pharmaceutical composition of claim 17, wherein the β-lactam antibiotic is selected from penems and carbapenems.

23. The pharmaceutical composition of claim 22, wherein the β-lactam antibiotic is a carbapenem selected from imipenem or meropenem.

24. The pharmaceutical composition of claim 17, wherein the ratio of the compound of formula I to the β-lactam antibiotic is from about 1:20 to about 1:1.

25. A pharmaceutical composition comprising
(a) a pharmaceutically effective amount of a compound having the formula

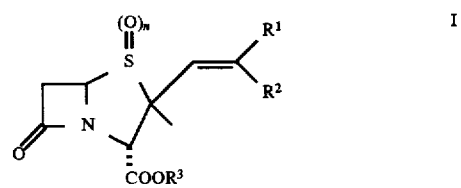

wherein one of R¹ and R² is —COR⁴, —CN, —CH₂R⁵, halogen, —CH=CHR⁶ or Q and the other is hydrogen or lower alkyl or both R¹ and R² together form a γ-lactam ring, R³ is hydrogen, lower alkyl, aryl-alkyl, allyl or a residue which is cleavable in vivo, R⁴ is lower alkyl, benzyloxy, amino, lower alkylamino or lower alkyl-lower alkoxyamino, R⁵ is —OCONHR⁷, —OCONH₂ or a five- or six-membered hetero-aromatic ring which contains at least one heteroatom selected from N, S and O and which is linked via a nitrogen atom, R⁶ is —CN or CHO, R⁷ is —COCH₂Cl, Q is a five- or six-membered hetero-aromatic ring which contains at least one heteroatom selected from N, S and O and n is 2, and the pharmaceutically compatible salts thereof and (b) an antibacterial effective amount of a β-lactam antibiotic, and their pharmaceutically compatible salts, and a pharmaceutically acceptable carrier.

26. The pharmaceutical composition of claim 25, wherein the β-lactam antibiotic is selected from penicillins, cephalosporins, and penems and carbapenems.

27. The pharmaceutical composition of claim 26, wherein the β-lactam antibiotic is a penicillin.

28. The pharmaceutical composition of claim 27, wherein the penicillin is selected from the group piperacillin, mezlocillin, azlocillin, apalcillin, benzylpenicillin, phenoxymethylpenicillin, carbenicillin, methicillin, propicillin, tricarcillin, ampicillin, amoxicillin, mecillinam, aspoxicillin, azidocillin, bacampicillin, carfecillin sodium, carindacillin, clometocillin, cloxacillin, cyclacillin, dicloxacillin, diphenicillin sodium, epicillin, fenbencillin, floxacillin, hetacillin, lenampicillin, metampicillin, nafcillin sodium, oxacillin, penamecillin, penethamate hydriodid, penicillin G benethamine, penicillin G benzathine, penicillin benzhydrylamine, penicillin G calcium, penicillin G hydrabamine, penicillin G potassium, penicillin G procaine, penicillin N, penicillin O, penimepicycline, phenethicillin potassium, pivampicillin, quinacillin, sulbenicillin, talampicillin, temocillin, and ticarcillin.

29. The pharmaceutial composition of claim 26, wherein the β-lactam antibiotic is a cephalosporin.

30. The pharmaceutical composition of claim 29, wherein the cephalosporin is selected from the group ceftriazone, ceftazidime, cefetamet, cefatamet pivoxil, cefotaxime, cefmenoxime, ceftizoxime, cefuroxime, cephaloridine, cephalotin, cefazolin, cephalexin, cefoxitin, cephacetrile, cefamandole, cephapirin, cephradine, cephaloglycine, cefpirome, cefepime, cefaclor, cefadroxil, cefatrizine, cefazedone, cefixime, cefodizime, cefonicid, cefoperazone, ceforanide, cefotiam, cefpimizole, cefpiramide, cefpodoxime proxetil, cefroxadine, cefsulodin, cefteram, ceftezole, ceftibuten, cefuzonam, cephalosporin C, and pivcefalexin.

31. The pharmaceutical composition of claim 26, wherein the β-lactam antibiotic is selected from penems and carbapenems.

32. The pharmaceutical composition of claim 31, wherein the β-lactam antibiotic is a carbapenem selected from imipenem or meropenem.

33. The pharmaceutical composition of claim 25, wherein the ratio of the compound of formula I to the β-lactam antibiotic is from about 1:20 to about 1:1.

34. A method of treating bacterial infections in a host in need of such therapy comprising administering (a) a pharmaceutically effective amount of a compound having the formula

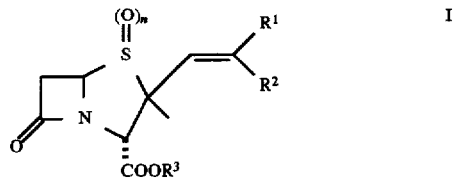

wherein one of R¹ and R² is —COR⁴, —CN, —CH₂R⁵, halogen, —CH=CHR⁶ or Q and the other is hydrogen or lower alkyl or both R¹ and R² together form a γ-lactam ring, R₃ is hydrogen, lower alkyl, aryl-alkyl, allyl or a residue which is cleavable in vivo, R₄ is lower alkyl, benzyloxy, amino, lower alkylamino or lower alkyl-lower alkoxyamino, R₅ is —OCONHR⁷, —OCONH₂ or a five- or six-membered hetero-aromatic ring which contains at least one heteroatom selected from N, S and O and which is linked via a nitrogen atom, R⁶ is —CN or —CHO, R⁷ is -COCH₂Cl, Q is a five- or six-membered hetero-aromatic ring which contains at least one heteroatom selected from N, S and O and n is 2, and the pharmaceutically compatible salts thereof and (b) an antibacterial effective amount of a β-lactam antibiotic, and their pharmaceutically compatible salts, and a pharmaceutically acceptable carrier.

35. The method of claim 34, wherein the β-lactam antibiotic is selected from penicillins, cephalosporins, and penems and carbapenems.

36. The method of claim 35, wherein the β-lactam antibiotic is a penicillin.

37. The method of claim 36, wherein the pencillin is selected from the group piperacillin, mezlocillin, azlocillin, apalcillin, benzylpenicillin, phenoxymethylpenicillin, carbenicillin, methicillin, propicillin, tricarcillin, ampicillin, amoxicillin, mecillinam, aspoxicillin, azidocillin, bacampicillin, carfecillin sodium, carindacillin, clometocillin, cloxacillin, cyclacillin, dicloxacillin, diphenicillin sodium, epicillin, fenbencillin, floxacillin, hetacillin, lenampicillin, metampicillin, nafcillin sodium, oxacillin, penamecillin, penethamate hydriodid, penicillin G benethamine, penicillin G benzathine, penicillin benzhydrylamine, penicillin G calcium, penicillin G hydrabamine, penicillin G potassium, penicillin G procaine, penicillin N, penicillin O, penimepicycline, phenethicillin potassium, pivampicillin, quinacillin, sulbenicillin, talampicillin, temocillin, and ticarcillin.

38. The method of claim 35, wherein the β-lactam antibiotic is a cephalosporin.

39. The method of claim 38, wherein the cephalosporin is selected from the group ceftriazone, ceftazidime, cefetamet, cefatamet pivoxil, cefotaxime, cefmenoxime, ceftizoxime, cefuroxime, cephaloridine, cephalotin, cefazolin, cephalexin, cefoxitin, cephacetrile, cefamandole, cephapirin, cephradine, cephaloglycine, cefpirome, cefepime, cefaclor, cefadroxil, cefatrizine, cefazedone, cefixime, cefodizime, cefonicid, cefoperazone, ceforanide, cefotiam, cefpimizole, cefpifamide, cefpodoxime proxetil, cefroxadine, cefsulodin, cefteram, ceftezole, ceftibuten, cefuzonam, cephalosporin C, and pivcefalexin.

40. The method of claim 35, wherein the β-lactam antibiotic is selected from penems and carbapenems.

41. The method of claim 40, wherein the β-lactam antibiotic is a carbapenem selected from imipenem or meropenem.

42. The method of claim 34, wherein the ratio of the compound of formula I to the β-lactam antibiotic is from about 1:20 to about 1:1.

43. A method of controlling bacterial infections in a host in need of such therapy comprising administering (a) an amount of a compound having the formula wherein one of $R^1$ and $R^2$ is —$COR^4$, —CN, —$CH_2R^5$, halogen, —CH=$CHR^6$ or Q and the other is hydrogen or lower alkyl or both $R^1$ and $R^2$ together form a γ-lactam ring, $R^3$ is hydrogen, lower alkyl, aryl-alkyl, allyl or a residue which is cleavable in vivo, $R^4$ is lower alkyl, benzyloxy, amino, lower alkylamino or lower alkyl-lower alkoxyamino, $R^5$ is —$OCONHR^7$, —$OCONH^2$ or a five- or six-membered hetero-aromatic ring which contains at least one heteroatom selected from N, S and O and which is linked via a nitrogen atom, $R^6$ is —CN or —CHO, $R^7$ is —$COCH_2Cl$, Q is a five- or six-membered hetero-aromatic ring which contains at least one heteroatom selected from N, S and O and n is 2, and the pharmaceutically compatible salts thereof which is effective in controlling bacterial infections, and (b) an antibacterial effective amount of a b-lactam antibiotic, and their pharmaceutically compatible salts, and a pharmaceutically acceptable carrier.

44. The method of claim 43, wherein the β-lactam antibiotic is selected from penicillins, cephalosporins, and penems and carbapenems.

45. The method of claim 43, wherein the ratio of the compound of formula I to the β-lactam antibiotic is from about 1:20 to about 1:1.

* * * * *

UNITED STATES PATENT AND TRADEMARK OFFICE
CERTIFICATE OF CORRECTION

PATENT NO. : 5,637,579
DATED : June 10, 1997
INVENTOR(S) : Christian Hubschwerlen, Hans Richter, Jean-Luc Specklin It is certified that error appears in the above-indentified patent and that said Letters Patent is hereby corrected as shown below:

In claim 2, column 30, line 57, delete "$R_2$" and insert therefor -- $R^2$ --.

In claim 14, column 31, line 35, delete "3 S" and insert therefor -- 3S --.

*In claim 15, column 31, line 59, delete "R1 and R2" and insert therefor -- $R^1$ and $R^2$ --.

*In claim 34, column 34, line 18, delete "$R_3$" and insert therefor -- $R^3$ --.

*In claim 34, column 34, line 20, delete "$R_4$" and insert therefor -- $R^4$ --.

*In claim 34, column 34, line 22, delete "$R_5$" and insert therefor -- $R^5$ --.

*In claim 43, column 36, line 14, delete "b-lactam" and insert therefor -- B-lactam --.

Signed and Sealed this

Thirtieth Day of September, 1997

Attest:

Attesting Officer

BRUCE LEHMAN

Commissioner of Patents and Trademarks